United States Patent
Potier et al.

(10) Patent No.: US 8,084,196 B2
(45) Date of Patent: Dec. 27, 2011

(54) METHOD FOR THE IN VITRO SCREENING OF ANTI-CANCER COMPOUNDS THAT INHIBITS SK3 ACTIVITY, AND SAID ANTI-CANCER COMPOUNDS

(75) Inventors: Marie Potier, Marcay (FR); Christophe Vandier, La Riche (FR); Virginie Joulin, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 248 days.

(21) Appl. No.: 12/376,181

(22) PCT Filed: Aug. 3, 2007

(86) PCT No.: PCT/EP2007/058052
§ 371 (c)(1),
(2), (4) Date: Feb. 3, 2009

(87) PCT Pub. No.: WO2008/015267
PCT Pub. Date: Feb. 7, 2008

(65) Prior Publication Data
US 2009/0311693 A1 Dec. 17, 2009

(30) Foreign Application Priority Data
Aug. 3, 2006 (EP) .................................... 06118417

(51) Int. Cl.
*C12Q 1/00* (2006.01)
(52) U.S. Cl. .......................................... 435/4
(58) Field of Classification Search .................. None
See application file for complete search history.

(56) References Cited

U.S. PATENT DOCUMENTS

| 6,165,719 A | 12/2000 | Chandy et al. |
| 2002/0028808 A1 | 3/2002 | Hansen |
| 2002/0165379 A1 | 11/2002 | Adelman et al. |
| 2005/0272093 A1 | 12/2005 | MacKinnon |
| 2006/0024677 A1 | 2/2006 | Morris et al. |

OTHER PUBLICATIONS

Terstappen et al (Neuropharmacology, 2001, 40: 772-783).*
Pedarzani et al (JBC, 2002, 277 (48): 46101-46109).*
Shridhar et al (Oncogene, 2004, 23: 2206-2215).*
Potier et al (Mol Cancer Ther, 2006, 5(11): 2946-2953).*
International search report in corresponding PCT/EP2007/058052.
Terstappen G C et al., "Pharmacological characterisation of the human small conductance calcium-activated potassium channel HSK3 reveals sensitivity to tricyclic antidepressants and antipsychotic phenothiazines", Neuropharmacology, Pergamon Press, vol. 40, No. 6, 2001, pp. 772-783, XP001147580.
Terstappen G C et al., "The antidepressant fluoxetine blocks the human small conductance calcium-activated potassium channels SK1, SK2 and SK3", Neuroscience Letters, Limerick, vol. 346, No. 1-2, Jun. 14, 2003, pp. 85-88, XP002302907.
Dale T J et al., "Partial apamin sensitivity of human small conductance CA2+-Activated K+ channels stably expressed in Chinese hamster ovary cells", Naunyn-Schmiedeberg's Archives of Pharmacology, Springer, vol. 366, No. 5, Nov. 2002, pp. 470-477, XP009055049.
Vanderwinden, J-M., et al., "Kit-negative fibroblast-like cells expressing SK3, a Ca2+-Activated K+ channel, in the gut musculature in health and disease", Cell Tissue Research, vol. 310, 2002, pp. 349-358, XP002428453.
Ouadid-Ahidouch H et al., "Cell-cycle-dependent expression of the large Ca<2+>-Activated K<+> channels in breast cancer cells", Biochemical and Biophysical Research Communications, Academic Press Inc., vol. 316, No. 1, Mar. 26, 2004, pp. 244-251, XP004493167.
Roger S et al., "Description and role in proliferation of iberiotoxin-sensitive currents in different human mammary epithelial normal and cancerous cells", Biochimica et Biophysica Acta., vol. 1667, No. 2, Dec. 15, 2004, pp. 190-199, XP004669640.
Potier, M., et al., "Identification of SK3 channel as a new mediator of breast cancer cell migration", Molecular Cancer Therapeutics, vol. 5, No. 11, Nov. 2006, pp. 2946-2953, XP002428454.

* cited by examiner

*Primary Examiner* — Sean Aeder
(74) *Attorney, Agent, or Firm* — Young & Thompson

(57) ABSTRACT

The present invention relates to methods for the in vitro screening of an anti-metastatic compound that inhibits activity, methods for determining in vitro the presence or absence of a metastatic cancer in a subject by quantifying SK3 activity, methods for the in vitro assessment of the progression of the metastatic property of a cancer by quantifying SK3.

2 Claims, 14 Drawing Sheets

A

B

A

B

SEQUENCE LISTING

<160> NUMBER OF SEQ ID NOS: 15

<210> SEQ ID NO 1
<211> LENGTH: 736
<212> TYPE: PRT
<213> ORGANISM: Homo sapiens

<400> SEQUENCE: 1

Met Asp Thr Ser Gly His Phe His Asp Ser Gly Val Gly Asp Leu Asp
1               5                   10                  15

Glu Asp Pro Lys Cys Pro Cys Pro Ser Ser Gly Asp Glu Gln Gln Gln
            20                  25                  30

Gln Gln Gln Gln Gln Gln Gln Gln Pro Pro Pro Pro Ala Pro Pro
        35                  40                  45

Ala Ala Pro Gln Gln Pro Leu Gly Pro Ser Leu Gln Pro Gln Pro Pro
    50                  55                  60

Gln Leu Gln Gln Gln Gln Gln Gln Gln Gln Gln Gln Gln Gln Gln Gln
65                  70                  75                  80

Gln Gln Gln Gln Gln Pro Pro His Pro Leu Ser Gln Leu Ala Gln Leu
                85                  90                  95

```
Gln Ser Gln Pro Val His Pro Gly Leu Leu His Ser Ser Pro Thr Ala
            100                 105                 110
Phe Arg Ala Pro Pro Ser Ser Asn Ser Thr Ala Ile Leu His Pro Ser
            115                 120                 125
Ser Arg Gln Gly Ser Gln Leu Asn Leu Asn Asp His Leu Leu Gly His
130                 135                 140
Ser Pro Ser Ser Thr Ala Thr Ser Gly Pro Gly Gly Ser Arg His
145                 150                 155                 160
Arg Gln Ala Ser Pro Leu Val His Arg Arg Asp Ser Asn Pro Phe Thr
                165                 170                 175
Glu Ile Ala Met Ser Ser Cys Lys Tyr Ser Gly Gly Val Met Lys Pro
            180                 185                 190
Leu Ser Arg Leu Ser Ala Ser Arg Arg Asn Leu Ile Glu Ala Glu Thr
            195                 200                 205
Glu Gly Gln Pro Leu Gln Leu Phe Ser Pro Ser Asn Pro Pro Glu Ile
210                 215                 220
Val Ile Ser Ser Arg Glu Asp Asn His Ala His Gln Thr Leu Leu His
225                 230                 235                 240
His Pro Asn Ala Thr His Asn His Gln His Ala Gly Thr Thr Ala Ser
                245                 250                 255
Ser Thr Thr Phe Pro Lys Ala Asn Lys Arg Lys Asn Gln Asn Ile Gly
            260                 265                 270
Tyr Lys Leu Gly His Arg Arg Ala Leu Phe Glu Lys Arg Lys Arg Leu
            275                 280                 285
Ser Asp Tyr Ala Leu Ile Phe Gly Met Phe Gly Ile Val Val Met Val
290                 295                 300
Ile Glu Thr Glu Leu Ser Trp Gly Leu Tyr Ser Lys Asp Ser Met Phe
305                 310                 315                 320
Ser Leu Ala Leu Lys Cys Leu Ile Ser Leu Ser Thr Ile Ile Leu Leu
                325                 330                 335
Gly Leu Ile Ile Ala Tyr His Thr Arg Glu Val Gln Leu Phe Val Ile
            340                 345                 350
Asp Asn Gly Ala Asp Asp Trp Arg Ile Ala Met Thr Tyr Glu Arg Ile
            355                 360                 365
Leu Tyr Ile Ser Leu Glu Met Leu Val Cys Ala Ile His Pro Ile Pro
            370                 375                 380
Gly Glu Tyr Lys Phe Phe Trp Thr Ala Arg Leu Ala Phe Ser Tyr Thr
385                 390                 395                 400
Pro Ser Arg Ala Glu Ala Asp Val Asp Ile Ile Leu Ser Ile Pro Met
                405                 410                 415
Phe Leu Arg Leu Tyr Leu Ile Ala Arg Val Met Leu Leu His Ser Lys
            420                 425                 430
Leu Phe Thr Asp Ala Ser Ser Arg Ser Ile Gly Ala Leu Asn Lys Ile
            435                 440                 445
Asn Phe Asn Thr Arg Phe Val Met Lys Thr Leu Met Thr Ile Cys Pro
            450                 455                 460
Gly Thr Val Leu Leu Val Phe Ser Ile Ser Leu Trp Ile Ala Ala
465                 470                 475                 480
Trp Thr Val Arg Val Cys Glu Arg Tyr His Asp Gln Gln Asp Val Thr
                485                 490                 495
Ser Asn Phe Leu Gly Ala Met Trp Leu Ile Ser Ile Thr Phe Leu Ser
            500                 505                 510
Ile Gly Tyr Gly Asp Met Val Pro His Thr Tyr Cys Gly Lys Gly Val
```

```
Cys Leu Leu Thr Gly Ile Met Gly Ala Gly Cys Thr Ala Leu Val Val
            515                 520                 525
Ala Val Val Ala Arg Lys Leu Glu Leu Thr Lys Ala Glu Lys His Val
    530                 535                 540
His Asn Phe Met Met Asp Thr Gln Leu Thr Lys Arg Ile Lys Asn Ala
545                 550                 555                 560
Ala Ala Asn Val Leu Arg Glu Thr Trp Leu Ile Tyr Lys His Thr Lys
                565                 570                 575
Leu Leu Lys Lys Ile Asp His Ala Lys Val Arg Lys His Gln Arg Lys
            580                 585                 590
Phe Leu Gln Ala Ile His Gln Leu Arg Ser Val Lys Met Glu Gln Arg
        595                 600                 605
Lys Leu Ser Asp Gln Ala Asn Thr Leu Val Asp Leu Ser Lys Met Gln
    610                 615                 620
Asn Val Met Tyr Asp Leu Ile Thr Glu Leu Asn Asp Arg Ser Glu Asp
625                 630                 635                 640
Leu Glu Lys Gln Ile Gly Ser Leu Glu Ser Lys Leu Glu His Leu Thr
                645                 650                 655
Ala Ser Phe Asn Ser Leu Pro Leu Leu Ile Ala Asp Thr Leu Arg Gln
            660                 665                 670
Gln Gln Gln Leu Leu Ser Ala Ile Ile Glu Ala Arg Gly Val Ser
        675                 680                 685
Val Ala Val Gly Thr Thr His Thr Pro Ile Ser Asp Ser Pro Ile Gly
    690                 695                 700
Val Ser Ser Thr Ser Phe Pro Thr Pro Tyr Thr Ser Ser Ser Cys
705                 710                 715                 720
                725                 730                 735

<210> SEQ ID NO 2
<211> LENGTH: 418
<212> TYPE: PRT
<213> ORGANISM: Homo sapiens

<400> SEQUENCE: 2

Met Phe Ser Leu Ala Leu Lys Cys Leu Ile Ser Leu Ser Thr Ile Ile
1               5                   10                  15

Leu Leu Gly Leu Ile Ile Ala Tyr His Thr Arg Glu Val Gln Leu Phe
            20                  25                  30

Val Ile Asp Asn Gly Ala Asp Asp Trp Arg Ile Ala Met Thr Tyr Glu
        35                  40                  45

Arg Ile Leu Tyr Ile Ser Leu Glu Met Leu Val Cys Ala Ile His Pro
    50                  55                  60

Ile Pro Gly Glu Tyr Lys Phe Phe Trp Thr Ala Arg Leu Ala Phe Ser
65                  70                  75                  80

Tyr Thr Pro Ser Arg Ala Glu Ala Asp Val Asp Ile Ile Leu Ser Ile
                85                  90                  95

Pro Met Phe Leu Arg Leu Tyr Leu Ile Ala Arg Val Met Leu Leu His
            100                 105                 110

Ser Lys Leu Phe Thr Asp Ala Ser Ser Arg Ser Ile Gly Ala Leu Asn
        115                 120                 125

Lys Ile Asn Phe Asn Thr Arg Phe Val Met Lys Thr Leu Met Thr Ile
    130                 135                 140

Cys Pro Gly Thr Val Leu Leu Val Phe Ser Ile Ser Leu Trp Ile Ile
145                 150                 155                 160

Ala Ala Trp Thr Val Arg Val Cys Glu Arg Tyr His Asp Gln Gln Asp
```

```
                    165                 170                 175
Val Thr Ser Asn Phe Leu Gly Ala Met Trp Leu Ile Ser Ile Thr Phe
                180                 185                 190

Leu Ser Ile Gly Tyr Gly Asp Met Val Pro His Thr Tyr Cys Gly Lys
            195                 200                 205

Gly Val Cys Leu Leu Thr Gly Ile Met Gly Ala Gly Cys Thr Ala Leu
        210                 215                 220

Val Val Ala Val Ala Arg Lys Leu Glu Leu Thr Lys Ala Glu Lys
225                 230                 235                 240

His Val His Asn Phe Met Met Asp Thr Gln Leu Thr Lys Arg Ile Lys
                245                 250                 255

Asn Ala Ala Asn Val Leu Arg Glu Thr Trp Leu Ile Tyr Lys His
            260                 265                 270

Thr Lys Leu Leu Lys Lys Ile Asp His Ala Lys Val Arg Lys His Gln
        275                 280                 285

Arg Lys Phe Leu Gln Ala Ile His Gln Leu Arg Ser Val Lys Met Glu
    290                 295                 300

Gln Arg Lys Leu Ser Asp Gln Ala Asn Thr Leu Val Asp Leu Ser Lys
305                 310                 315                 320

Met Gln Asn Val Met Tyr Asp Leu Ile Thr Glu Leu Asn Asp Arg Ser
                325                 330                 335

Glu Asp Leu Glu Lys Gln Ile Gly Ser Leu Glu Ser Lys Leu Glu His
            340                 345                 350

Leu Thr Ala Ser Phe Asn Ser Leu Pro Leu Leu Ile Ala Asp Thr Leu
        355                 360                 365

Arg Gln Gln Gln Gln Leu Leu Ser Ala Ile Ile Glu Ala Arg Gly
    370                 375                 380

Val Ser Val Ala Val Gly Thr Thr His Thr Pro Ile Ser Asp Ser Pro
385                 390                 395                 400

Ile Gly Val Ser Ser Thr Ser Phe Pro Thr Pro Tyr Thr Ser Ser Ser
                405                 410                 415

Ser Cys

<210> SEQ ID NO 3
<211> LENGTH: 426
<212> TYPE: PRT
<213> ORGANISM: Homo sapiens

<400> SEQUENCE: 3

Met Glu Arg Pro Ile Lys Asp Ser Met Phe Ser Leu Ala Leu Lys Cys
1               5                   10                  15

Leu Ile Ser Leu Ser Thr Ile Ile Leu Leu Gly Leu Ile Ile Ala Tyr
            20                  25                  30

His Thr Arg Glu Val Gln Leu Phe Val Ile Asp Asn Gly Ala Asp Asp
        35                  40                  45

Trp Arg Ile Ala Met Thr Tyr Glu Arg Ile Leu Tyr Ile Ser Leu Glu
    50                  55                  60

Met Leu Val Cys Ala Ile His Pro Ile Pro Gly Glu Tyr Lys Phe Phe
65                  70                  75                  80

Trp Thr Ala Arg Leu Ala Phe Ser Tyr Thr Pro Ser Arg Ala Glu Ala
                85                  90                  95

Asp Val Asp Ile Ile Leu Ser Ile Pro Met Phe Leu Arg Leu Tyr Leu
            100                 105                 110

Ile Ala Arg Val Met Leu Leu His Ser Lys Leu Phe Thr Asp Ala Ser
        115                 120                 125
```

```
Ser Arg Ser Ile Gly Ala Leu Asn Lys Ile Asn Phe Asn Thr Arg Phe
    130                 135                 140

Val Met Lys Thr Leu Met Thr Ile Cys Pro Gly Thr Val Leu Leu Val
145                 150                 155                 160

Phe Ser Ile Ser Leu Trp Ile Ile Ala Ala Trp Thr Val Arg Val Cys
                165                 170                 175

Glu Arg Tyr His Asp Gln Gln Asp Val Thr Ser Asn Phe Leu Gly Ala
                180                 185                 190

Met Trp Leu Ile Ser Ile Thr Phe Leu Ser Ile Gly Tyr Gly Asp Met
                195                 200                 205

Val Pro His Thr Tyr Cys Gly Lys Gly Val Cys Leu Leu Thr Gly Ile
    210                 215                 220

Met Gly Ala Gly Cys Thr Ala Leu Val Val Ala Val Val Ala Arg Lys
225                 230                 235                 240

Leu Glu Leu Thr Lys Ala Glu Lys His Val His Asn Phe Met Met Asp
                245                 250                 255

Thr Gln Leu Thr Lys Arg Ile Lys Asn Ala Ala Ala Asn Val Leu Arg
                260                 265                 270

Glu Thr Trp Leu Ile Tyr Lys His Thr Lys Leu Leu Lys Lys Ile Asp
                275                 280                 285

His Ala Lys Val Arg Lys His Gln Arg Lys Phe Leu Gln Ala Ile His
    290                 295                 300

Gln Leu Arg Ser Val Lys Met Glu Gln Arg Lys Leu Ser Asp Gln Ala
305                 310                 315                 320

Asn Thr Leu Val Asp Leu Ser Lys Met Gln Asn Val Met Tyr Asp Leu
                325                 330                 335

Ile Thr Glu Leu Asn Asp Arg Ser Glu Asp Leu Glu Lys Gln Ile Gly
                340                 345                 350

Ser Leu Glu Ser Lys Leu Glu His Leu Thr Ala Ser Phe Asn Ser Leu
                355                 360                 365

Pro Leu Leu Ile Ala Asp Thr Leu Arg Gln Gln Gln Gln Gln Leu Leu
    370                 375                 380

Ser Ala Ile Ile Glu Ala Arg Gly Val Ser Val Ala Val Gly Thr Thr
385                 390                 395                 400

His Thr Pro Ile Ser Asp Ser Pro Ile Gly Val Ser Ser Thr Ser Phe
                405                 410                 415

Pro Thr Pro Tyr Thr Ser Ser Ser Ser Cys
                420                 425

<210> SEQ ID NO 4
<211> LENGTH: 751
<212> TYPE: PRT
<213> ORGANISM: Homo sapiens

<400> SEQUENCE: 4

Met Asp Thr Ser Gly His Phe His Asp Ser Gly Val Gly Asp Leu Asp
1               5                   10                  15

Glu Asp Pro Lys Cys Pro Cys Pro Ser Ser Gly Asp Glu Gln Gln Gln
                20                  25                  30

Gln Gln Gln Gln Gln Gln Gln Gln Pro Pro Pro Ala Pro Pro
            35                  40                  45

Ala Ala Pro Gln Gln Pro Leu Gly Pro Ser Leu Gln Pro Gln Pro Pro
    50                  55                  60

Gln Leu Gln Gln Gln Gln Gln Gln Gln Gln Gln Gln Gln Gln Gln Gln
65                  70                  75                  80
```

```
Gln Gln Gln Gln Gln Pro Pro His Pro Leu Ser Gln Leu Ala Gln Leu
                 85                  90                  95

Gln Ser Gln Pro Val His Pro Gly Leu Leu His Ser Ser Pro Thr Ala
            100                 105                 110

Phe Arg Ala Pro Pro Ser Ser Asn Ser Thr Ala Ile Leu His Pro Ser
        115                 120                 125

Ser Arg Gln Gly Ser Gln Leu Asn Leu Asn Asp His Leu Leu Gly His
    130                 135                 140

Ser Pro Ser Ser Thr Ala Thr Ser Gly Pro Gly Gly Ser Arg His
145                 150                 155                 160

Arg Gln Ala Ser Pro Leu Val His Arg Arg Asp Ser Asn Pro Phe Thr
                165                 170                 175

Glu Ile Ala Met Ser Ser Cys Lys Tyr Ser Gly Gly Val Met Lys Pro
            180                 185                 190

Leu Ser Arg Leu Ser Ala Ser Arg Arg Asn Leu Ile Glu Ala Glu Thr
        195                 200                 205

Glu Gly Gln Pro Leu Gln Leu Phe Ser Pro Ser Asn Pro Pro Glu Ile
    210                 215                 220

Val Ile Ser Ser Arg Glu Asp Asn His Ala His Gln Thr Leu Leu His
225                 230                 235                 240

His Pro Asn Ala Thr His Asn His Gln His Ala Gly Thr Thr Ala Ser
                245                 250                 255

Ser Thr Thr Phe Pro Lys Ala Asn Lys Arg Lys Asn Gln Asn Ile Gly
            260                 265                 270

Tyr Lys Leu Gly His Arg Arg Ala Leu Phe Glu Lys Arg Lys Arg Leu
        275                 280                 285

Ser Asp Tyr Ala Leu Ile Phe Gly Met Phe Gly Ile Val Val Met Val
    290                 295                 300

Ile Glu Thr Glu Leu Ser Trp Gly Leu Tyr Ser Lys Asp Ser Met Phe
305                 310                 315                 320

Ser Leu Ala Leu Lys Cys Leu Ile Ser Leu Ser Thr Ile Ile Leu Leu
                325                 330                 335

Gly Leu Ile Ile Ala Tyr His Thr Arg Glu Val Gln Leu Phe Val Ile
            340                 345                 350

Asp Asn Gly Ala Asp Asp Trp Arg Ile Ala Met Thr Tyr Glu Arg Ile
        355                 360                 365

Leu Tyr Ile Ser Leu Glu Met Leu Val Cys Ala Ile His Pro Ile Pro
    370                 375                 380

Gly Glu Tyr Lys Phe Phe Trp Thr Ala Arg Leu Ala Phe Ser Tyr Thr
385                 390                 395                 400

Pro Ser Arg Ala Glu Ala Asp Val Asp Ile Ile Leu Ser Ile Pro Met
                405                 410                 415

Phe Leu Arg Leu Tyr Leu Ile Ala Arg Val Met Leu Leu His Ser Lys
            420                 425                 430

Leu Phe Thr Asp Ala Ser Ser Arg Ser Ile Gly Ala Leu Asn Lys Ile
        435                 440                 445

Asn Phe Asn Thr Arg Phe Val Met Lys Thr Leu Met Thr Ile Cys Pro
    450                 455                 460

Gly Thr Val Leu Leu Val Phe Ser Ile Ser Leu Trp Ile Ile Ala Ala
465                 470                 475                 480

Trp Thr Val Arg Val Cys Glu Ser Pro Glu Ser Pro Ala Gln Pro Ser
                485                 490                 495

Gly Ser Ser Leu Pro Ala Trp Tyr His Asp Gln Gln Asp Val Thr Ser
```

```
                          500                 505                 510
Asn Phe Leu Gly Ala Met Trp Leu Ile Ser Ile Thr Phe Leu Ser Ile
        515                 520                 525

Gly Tyr Gly Asp Met Val Pro His Thr Tyr Cys Gly Lys Gly Val Cys
    530                 535                 540

Leu Leu Thr Gly Ile Met Gly Ala Gly Cys Thr Ala Leu Val Val Ala
545                 550                 555                 560

Val Val Ala Arg Lys Leu Glu Leu Thr Lys Ala Glu Lys His Val His
                565                 570                 575

Asn Phe Met Met Asp Thr Gln Leu Thr Lys Arg Ile Lys Asn Ala Ala
            580                 585                 590

Ala Asn Val Leu Arg Glu Thr Trp Leu Ile Tyr Lys His Thr Lys Leu
        595                 600                 605

Leu Lys Lys Ile Asp His Ala Lys Val Arg Lys His Gln Arg Lys Phe
    610                 615                 620

Leu Gln Ala Ile His Gln Leu Arg Ser Val Lys Met Glu Gln Arg Lys
625                 630                 635                 640

Leu Ser Asp Gln Ala Asn Thr Leu Val Asp Leu Ser Lys Met Gln Asn
                645                 650                 655

Val Met Tyr Asp Leu Ile Thr Glu Leu Asn Asp Arg Ser Glu Asp Leu
            660                 665                 670

Glu Lys Gln Ile Gly Ser Leu Glu Ser Lys Leu Glu His Leu Thr Ala
        675                 680                 685

Ser Phe Asn Ser Leu Pro Leu Leu Ile Ala Asp Thr Leu Arg Gln Gln
    690                 695                 700

Gln Gln Gln Leu Leu Ser Ala Ile Ile Glu Ala Arg Gly Val Ser Val
705                 710                 715                 720

Ala Val Gly Thr Thr His Thr Pro Ile Ser Asp Ser Pro Ile Gly Val
                725                 730                 735

Ser Ser Thr Ser Phe Pro Thr Pro Tyr Thr Ser Ser Ser Cys
            740                 745                 750

<210> SEQ ID NO 5
<211> LENGTH: 23
<212> TYPE: DNA
<213> ORGANISM: Artificial Sequence
<220> FEATURE:
<223> OTHER INFORMATION: Synthetic sense polynucleotide

<400> SEQUENCE: 5
gaaagcgacu gagugacuad tdt                                          23

<210> SEQ ID NO 6
<211> LENGTH: 22
<212> TYPE: DNA
<213> ORGANISM: Artificial Sequence
<220> FEATURE:
<223> OTHER INFORMATION: Synthetic anti-sense sense polynucleotide

<400> SEQUENCE: 6
uagucacuca gucgcuucdt dt                                           22

<210> SEQ ID NO 7
<211> LENGTH: 23
<212> TYPE: DNA
<213> ORGANISM: Artificial Sequence
<220> FEATURE:
<223> OTHER INFORMATION: Synthetic sense polynucleotide

<400> SEQUENCE: 7
```

```
ccauuccugg cgaguacaad tdt                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic anti-sense sense polynucleotide

<400> SEQUENCE: 8
uuguacucgc caggaauggd tdt                                              23

<210> SEQ ID NO 9
<211> LENGTH: 20
<212> TYPE: DNA
<213> ORGANISM: Homo sapiens

<400> SEQUENCE: 9
gacttggcaa agacccagaa                                                  20

<210> SEQ ID NO 10
<211> LENGTH: 20
<212> TYPE: DNA
<213> ORGANISM: Homo sapiens

<400> SEQUENCE: 10
ccgctcagca ttgtaagtga                                                  20

<210> SEQ ID NO 11
<211> LENGTH: 20
<212> TYPE: DNA
<213> ORGANISM: Homo sapiens

<400> SEQUENCE: 11
tggacactca gctcaccaag                                                  20

<210> SEQ ID NO 12
<211> LENGTH: 20
<212> TYPE: DNA
<213> ORGANISM: Homo sapiens

<400> SEQUENCE: 12
gttccatctt gacgctcctc                                                  20

<210> SEQ ID NO 13
<211> LENGTH: 22
<212> TYPE: DNA
<213> ORGANISM: Homo sapiens

<400> SEQUENCE: 13
ggcagaccga gatgaatcct ca                                               22

<210> SEQ ID NO 14
<211> LENGTH: 21
<212> TYPE: DNA
<213> ORGANISM: Homo sapiens

<400> SEQUENCE: 14
caggtccagg ggtcttggtc c                                                21

<210> SEQ ID NO 15
<211> LENGTH: 25
<212> TYPE: DNA
<213> ORGANISM: Artificial Sequence
```

```
<220> FEATURE:
<223> OTHER INFORMATION: Synthetic siRNA

<400> SEQUENCE: 15
auaacuguau cgaauguuau gagcc                                              25
```

METHOD FOR THE IN VITRO SCREENING OF ANTI-CANCER COMPOUNDS THAT INHIBITS SK3 ACTIVITY, AND SAID ANTI-CANCER COMPOUNDS

FIELD OF THE INVENTION

The present invention relates to methods for inhibiting the migratory, invasive and metastatic properties of cells expressing SK3 for the treatment of cancers such as melanomas, and breast cancers. The invention further relates to drug screening methods designed to identify compounds that inhibit SK3 activity and the use of such compounds in the treatment of cancers.

BACKGROUND OF THE INVENTION

Despite enormous investments of financial and human resources, cancer remains one of the major causes of death. Current cancer therapies cure only about fifty percent of the patients who develop a malignant tumor. In most human malignancies, metastasis is the major cause of death.

Metastasis is the formation of a secondary tumor colony at a distant site. It is a multistep process of which tumor invasion is an early event. Tumor cells locally invade host tissue barriers, such as the epithelial basement membrane, to reach the interstitial stroma, where they gain access to blood vessels ("hematogenous metastasis") or lymphatic channels for further dissemination. After invading the endothelial layer of a vessel wall, the circulating tumor cells are dislodged into the circulation and arrested in the precapillary venules of the target organ by adherence to endothelial cell lumenal surfaces, or exposed basement membranes. The tumor cells again invade the vascular wall to enter the organ parenchyma. Finally, the extravasated tumor cell grows in a tissue different from where it originated.

As cancer treatments using radiation and/or chemotherapies become more effective, and more people live for longer periods of time following treatment, cancer survivors are faced with a significant risk of developing therapy-induced secondary tumors.

Because of the inherent mutagenicity of ionizing radiation and most anti-cancer drugs, investigators predicted that therapy-induced secondary tumors would become a major health issue.

Due to the difficulties in the current approaches to the treatment and prevention of metastases, there is a need in the art for novel therapeutically useful compounds for preventing individuals from the occurrence of metastasis in the course of a cancer.

Additionally, In most human malignancies, distant metastases are often too small to be detected at the time the primary tumor is treated. Furthermore, widespread initiation of metastatic colonies usually occurs before clinical symptoms of metastatic disease are evident. The size and age variation in metastases, their dispersed anatomical location, and their heterogeneous composition are all factors that hinder surgical removal and limit the concentration of anti-cancer drugs that can be delivered to the metastatic colonies.

Accordingly, there is still a need in the art for methods that will allow the one skilled in the art to determine the status of progression of cancers in patients so as to enable a precise prognosis of the evolution of the disease, including the occurrence of metastasis, and also to enable a precise monitoring of the therapeutical treatment which may be the more beneficial to the patient, once taken into account the progression status of the cancer. For example, there is a need in the art for novel biological markers which are indicative of the occurrence of a cancer. These novel biological markers might be used in combination with one or several already known markers.

The present invention fulfils these needs and further provides other related advantages.

SUMMARY OF THE INVENTION

The invention is firstly directed to a method for the in vitro screening of an anti-metastatic compound that inhibits SK3 activity comprising:
(i) contacting a cell expressing a functional SK3 with a candidate compound and measuring the level of SK3 activity;
(ii) comparing the level of SK3 activity which is measured at step (i) with the level of SK3 activity which is measured when step (i) is performed in the absence of said candidate compound,
wherein a decrease of SK3 activity in the presence of the candidate compound indicates that the candidate consists of an anti-metastatic compound.

It also relates to a method for determining in vitro the presence or absence of a metastatic cancer in a subject, comprising the steps of:
(i) quantifying SK3 activity in a test sample comprising cancerous cells of a specific tissue type obtained from a cancerous subject,
(ii) comparing the level of SK3 activity which is quantified at step (i) with the level of SK3 activity which is quantified when step (i) is performed in a control sample comprising non-cancerous cells or non-metastatic cancerous cells of the same tissue type,
wherein a greater level of SK3 activity in the test sample, compared to the control sample, indicates the presence of a metastatic cancer in the cancerous subject, and a level of SK3 activity in the test sample identical to, or lower than the level of SK3 activity quantified in the control sample, indicates the absence of a metastatic cancer in the cancerous subject.

The invention also deals with a method for the in vitro assessment of the progression of the metastatic property of a cancer in a subject, wherein said method comprises the steps of:
(i) quantifying SK3 activity in a sample comprising cancerous cells of a specific tissue type obtained from a cancerous subject, at a first time point,
(ii) quantifying SK3 activity in a sample comprising cancerous cells of the same tissue type, obtained from said cancerous subject, at a subsequent time point,
wherein a greater level of SK3 activity at step (ii), compared to step (i), indicates an increase in the metastatic property of the cancer from the subject, and a lower level of SK3 activity at step (ii), compared to step (i), indicates a decrease in the metastatic property of the cancer from the subject.

B, C—Current-density was obtained by dividing the averaged steady-state current elicited at +26 mV (recorded during the latest 50 ms of the pulse) by the respective cell capacitance. Membrane capacitance was calculated by integrating the capacitive current measured during a 10 mV voltage step. Results expressed as mean±S.E.M. of the inhibitory effects of apamin (n=4), TEA (n=7), 4-AP (n=8) and TEA plus 4-AP (n=3).

D—Variations of membrane potential recorded in control conditions (PSS without drugs, n=11) and in presence of TEA (n=7), 4-AP (n=8) and TEA plus 4-AP (n=3). Membrane potential was measured in current-clamp mode (I=0) just after the disruption of the patch membrane. Results expressed as mean±S.E.M. * significantly different from control at p<0.05.

Figure 3:
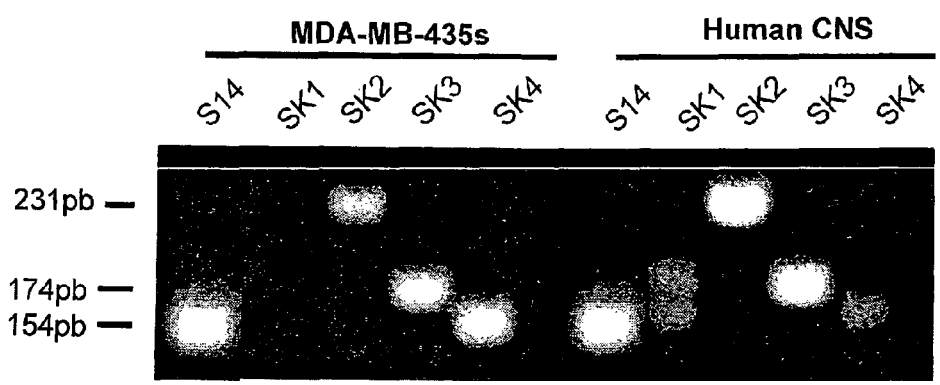
Figure 3:
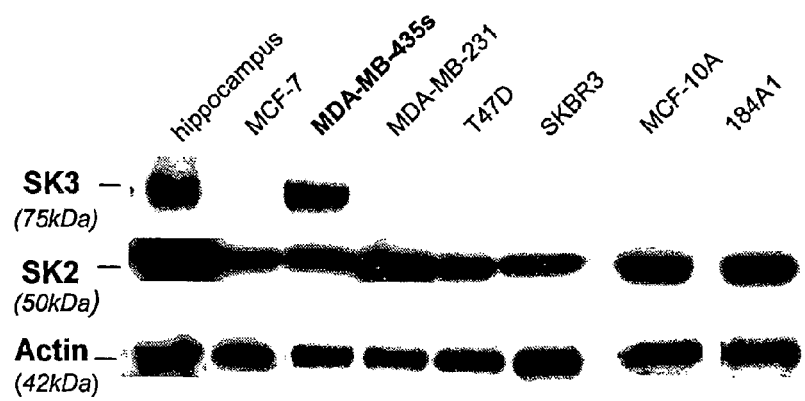

FIG. 3: SK3 protein is expressed in MDA-MB-435s and in tumor breast tissue. A—Detection of SK channels mRNA (SK1, SK2, SK3 and SK4) in MDA-MB-435s. RT-PCR was performed in MDA-MB-435s cells and in human CNS cDNA as a positive control. Primers used for the RT-PCR experiments are listed in the Materials and Methods section. Representative examples of three separate experiments.

B—Representative Western blot pattern of SK2 and SK3 protein expression in cancerous and non cancerous mammary epithelial cell lines. Lysates of human mammary cancer cell lines (MDA-MB-435s, MDA-MB-231, MCF-7, T47D and SKBR3), of non-cancerous mammary epithelial cells lines (184A1, MCF-10A) and of rat hippocampus tissue (used as positive control) were prepared in lysis buffer (SDS 5%, protease inhibitors 1%, PMSF 200 mM). Cells extracts were subjected to electrophoresis on SDS-polyacrylamide gel under reducing conditions and the signal was detected by ECL. Results were provided in triplicate.

FIG. 4: SK3 gene transcript destruction decreases migration of MDA-MB-435s cells and SK3 gene expression increases migration of 184A1 cells.

A—Top, Western blot patterns showing the silencing effect on the expression of SK3 protein—of two siRNAs designed against SK3 mRNA. Cells were transfected with siRNA-lipofectamine complexes for 24 h, 48 h and 72 h. A scrambled-siRNA was used as negative control. SiRNA oligonucleotide sequences are listed in the Materials and Methods section. Bottom, Histograms showing the inhibitory effect on MDA-MB-4345s cell migration after 24 h, 48 h and 72 h siRNA transfection with or without 10 nM apamin. Results from two separate experiments performed in triplicate are expressed as mean±S.E.M. Normalization of cell number performed as described in the legend of FIG. 1. Note that the cells have lost their sensitivity for apamin after siRNA transfection, indicating a specific effect on SK3 protein.

B—Top, Western blot patterns showing the expression of the SK3 protein channel after transient transfection of SK3-pTracer-CMV2 plasmid (SK3 transfection) or empty vector (control transfection) in cancerous (MCF-7) and non-cancerous (184A1) mammary epithelial cell lines. Bottom, histograms showing the number of migrating cells after transient transfection, with or without 10 nM apamin. Results from two separate experiments performed in triplicate are expressed as mean±S.E.M. Note that SK3-transfected cells have gained a sensitivity to apamin indicating a specific expression of SK3 channel.

Figure 5:
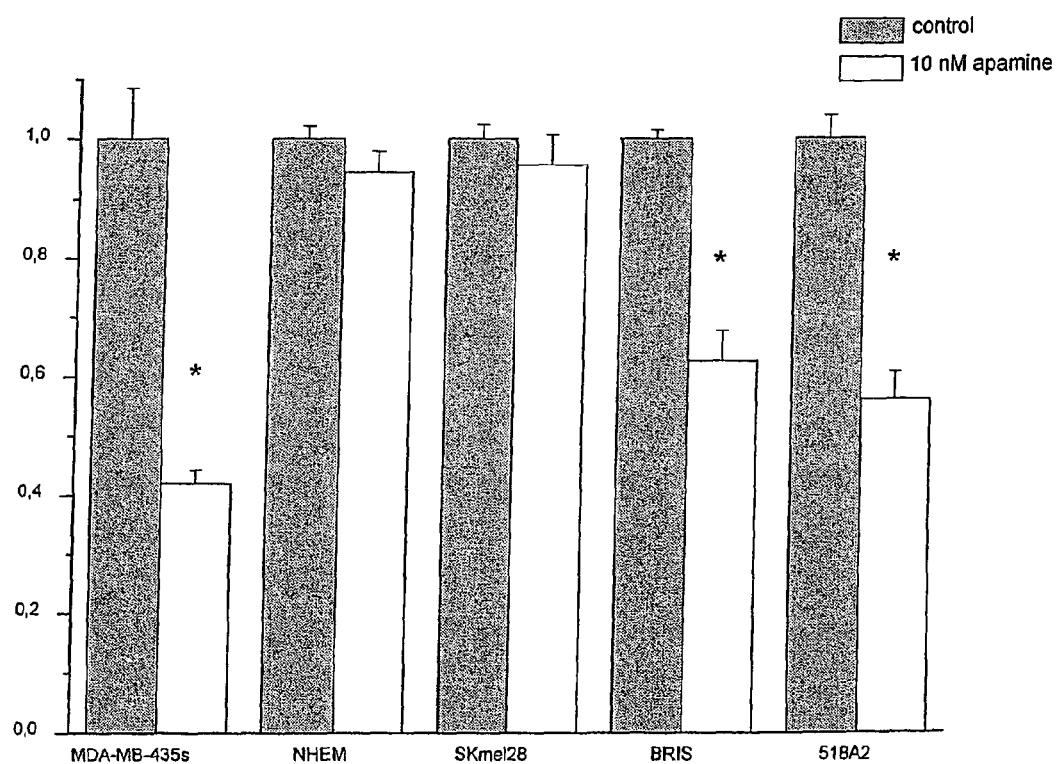

FIG. 5: Involvement of SKCa channels in melanoma and melanocyte migration.

Histograms showing the effect of 10 nM apamin on cell migration (FIG. 5A). Cells were seeded at 40000 in a cell culture insert in DMEM with 5% FBS±apamin. The lower compartment of the insert contained DMEM with 10% FBS as a chemoattractant±apamin. After 24 h, cells of the lower side were stained with hematoxylin (FIG. 5B, right) and counted. The normalized cell number corresponded to the ratio of total number of migrating cells in presence of apamin/total number of migrating cells in control experiments. The apamin concentration selected has no effect on cell proliferation and viability. Results from two separate experiments performed in triplicate are expressed as mean±S.E.M. * significantly different from control at p<0.05. Mammary cancer MDA-MB-435s cells were used as control cell. FIG. 5B—Pictures of 518A2 cells before and after 10 nM apamin treatment.

Figure 6:
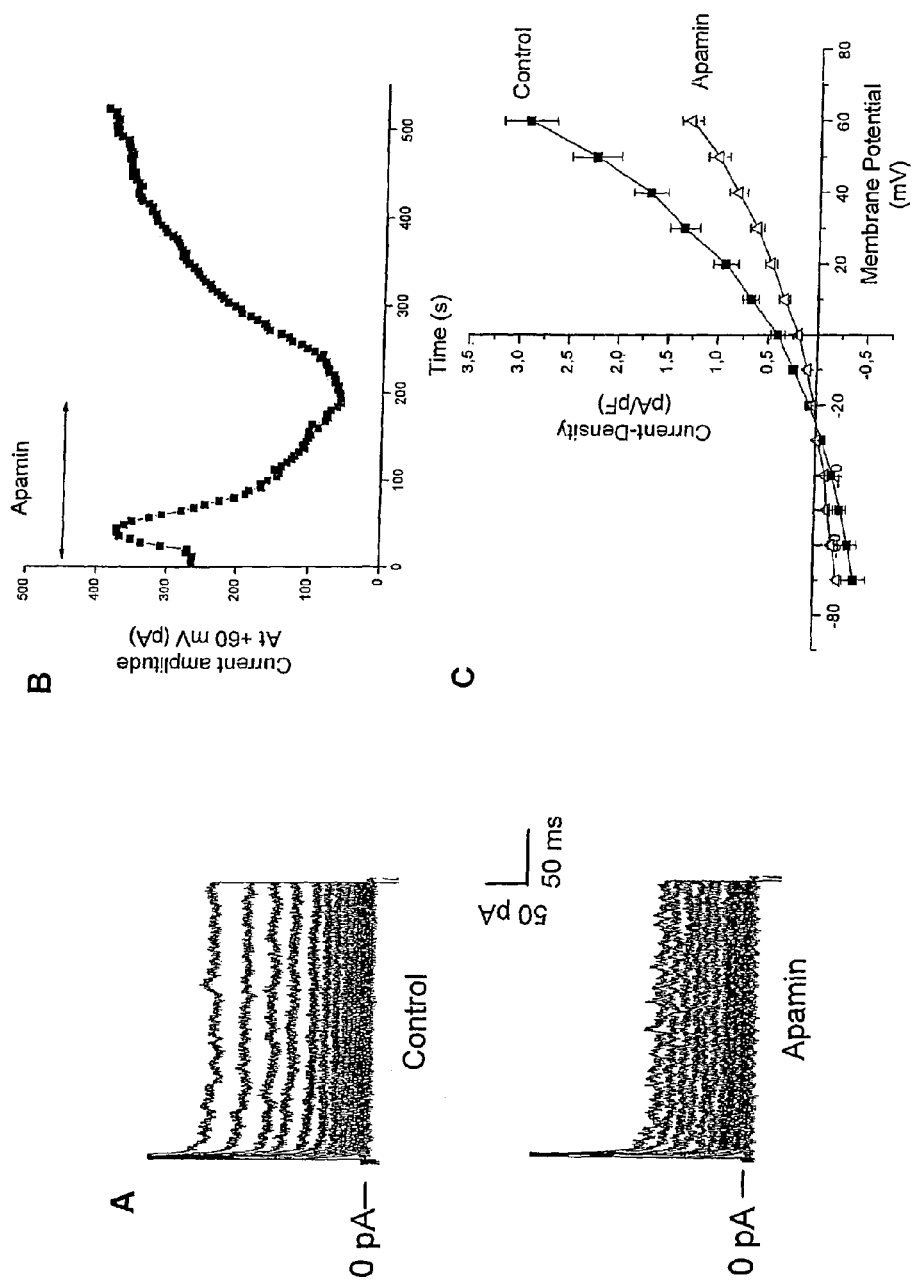

FIG. 6: Activity of SKCa channels in 518A2 cells.

FIG. 6A—Example of whole-cell macroscopic K+ currents recorded in one cell without (control) or with apamin in the external medium. Currents were generated by stepwise 10 mV depolarizing pulses (400 ms duration; 5 sec intervals) from a constant holding potential of −70 mV up to +60 mV. Signals were filtered at 1 kHz and digitized at 10 kHz.

FIG. 6B—Current amplitude recorded during the latest 50 ms of the pulse was obtained at +60 mV.

FIG. 6C—Current density-voltage relation showing that apamin (10 nM) decreased net outward current amplitude of 518A2 cells. Membrane capacitance was calculated by integrating the capacitive current measured during a 10 mV voltage step. Current-density was obtained by dividing current amplitude recorded during the latest 50 ms of the pulse by cell capacitance.

Figure 7:
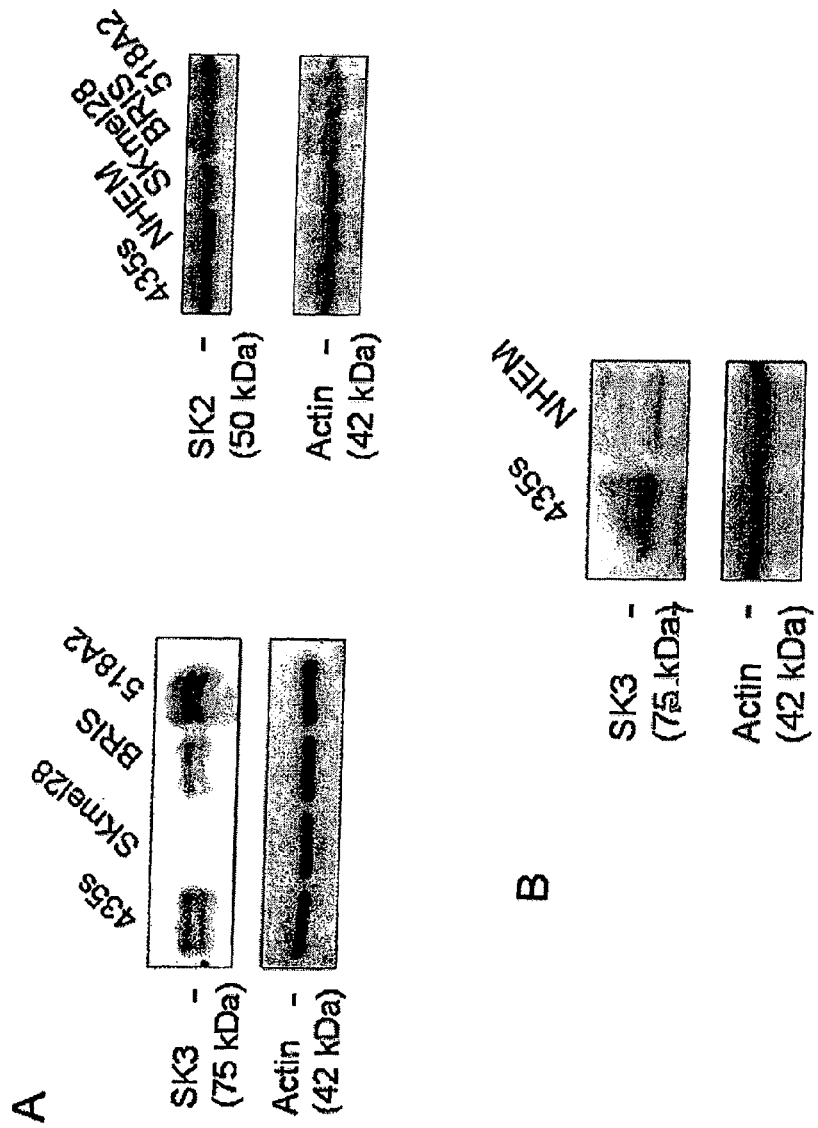

FIG. 7: SK3 protein is expressed in melanoma cells and melanocyte. Representative Western blot pattern of SK2 and SK3 protein expression in melanoma (FIG. 7A) and melanocyte (FIG. 7B). Lysates of melanoma cells (SKmel28, BRIS and 518A2), of melanocyte (NHEM) and of MDA-MB-435s cells (used as control cells) were prepared in lysis buffer (SDS 5%, protease inhibitors 1%, PMSF 200 mM). Cell extracts were subjected to electrophoresis on SDS-polyacrylamide gel under reducing conditions and the signal was detected by ECL. Results were provided in triplicate.

Figure 8:
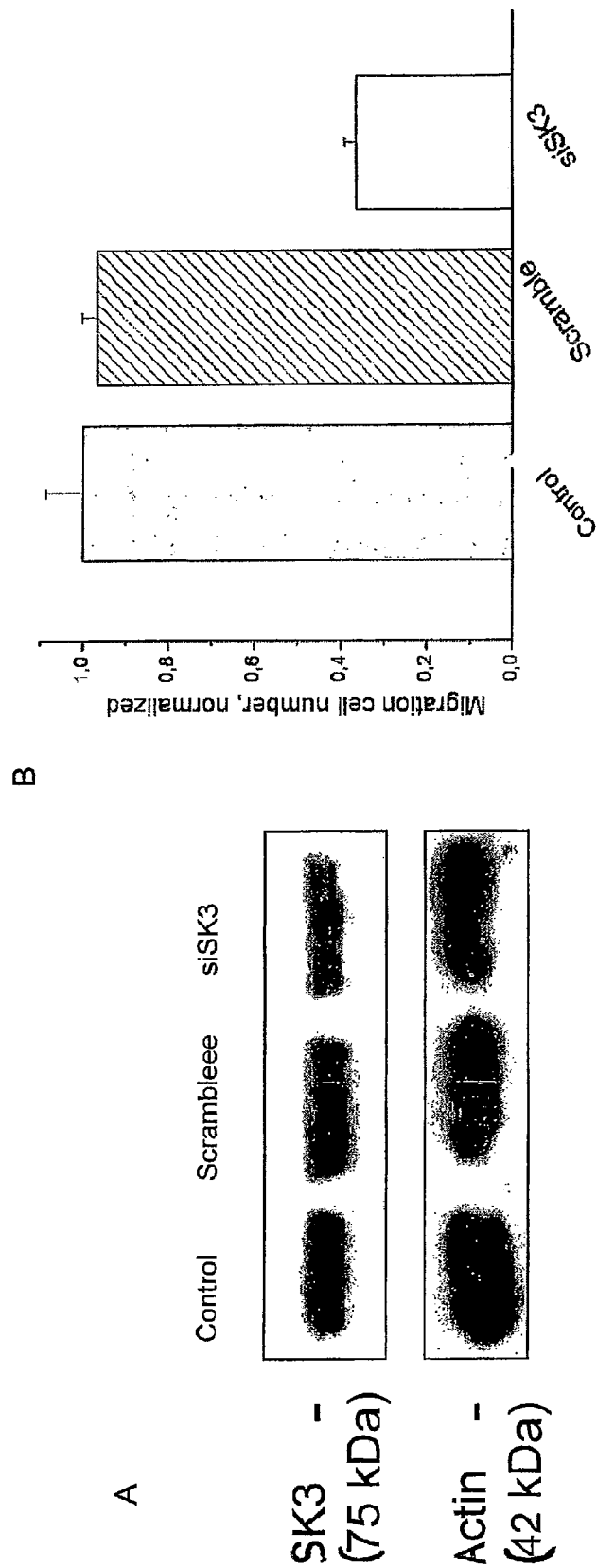

FIG. 8: SK3 gene transcript destruction decreases migration of 518A2 cells.

FIG. 8A—Western blot patterns showing the silencing effect on the expression of SK3 protein of two siRNAs designed against SK3 mRNA. Cells were transfected with siRNA-lipofectamine complexes for 48 h. A scrambled-siRNA was used as negative control. siRNA oligonucleotide sequences are listed in the Materials and Methods section.

FIG. 8B—Histograms showing the inhibitory effect on 518A2 cell migration 48 h of siRNA transfection.

DETAILED DESCRIPTION OF THE INVENTION

It has been shown according to the invention that a specific SK channel, namely SK3 is expressed in metastazing cancer cells, and that a straight correlation exists between SK3 activity and the property of cancer cells to migrate. Indeed, the inventors have shown that a decrease in SK3 activity abolishes cell migration of cancer cells, while a transient expression of SK3, increases migration of cancerous SK3-deficient cell lines. Accordingly, the inventors have shown that SK3 expression promote cell migration of cancer cells.

Furthermore, the inventors have shown that SK3 channel is solely expressed in tumor breast biopsies, and not in non-tumor breast biopsies.

The inventors have elucidated the mechanism underlying cell migration of metastazing cancer cells, which involves a regulation of membrane potential by SK3. It has been shown according to the invention that SK3 channels promote epithelial cell migration by increasing intracellular $Ca^{2+}$ concentration. More precisely, it has been shown according to the invention that SK3 channel is necessary and promotes cancerous mammary epithelial cell migration by hyperpolarizing their plasma membrane. Indeed, SK3 channels maintains a high level of intracellular $Ca^{2+}$ concentration in a highly metastazing cancerous mammary epithelial cell line, i.e. MDA-MB-435s.

Without wishing to be bound by any particular theory, the inventors believe that this could be explained by the presence of voltage-independent $Ca^{2+}$ channels through which $Ca^{2+}$ entry increases following membrane hyperpolarization. The increase of epithelial cell migration mediated by SK3 channel would therefore be the result of an increased $K^+$ efflux and subsequent shift of the membrane potential to more negative values, leading to $Ca^{2+}$ entry through voltage-independent $Ca^{2+}$ channels.

As shown in the examples herein, SK3 consists of a new marker of metastatic transformation of a variety of cancerous cells. For these cancerous cells, it has been shown the mediation of the SK3 expression in cell migration.

SK3 as a marker of cancerous cells metastatic transformation, has been shown notably through the use of a panel of SKCa blockers together with siRNA or overexpression approaches in the examples herein.

SK3 as a marker of cancerous cells metastatic transformation, has also been shown, in the examples herein, by the experimental demonstration of the deep involvement of the SK3 gene and protein expression in melanoma cell migration As cell migration is one of the main properties of metastatic cells, and constitutes a preliminary step before occurrence of a metastatic cancer, SK3 consists of a target for a new class of anticancer agents.

Then, compounds that inhibit SK3 activity, by acting on cell migration, can be used for preventing the occurrence of metastasis from primary cancers, or for treating metastatic properties of cancers.

Accordingly, the invention concerns a method for the in vitro screening of an anti-metastatic compound that inhibits SK3 activity comprising:
(i) contacting a cell expressing a functional SK3 with a candidate compound and measuring the level of SK3 activity;
(ii) comparing the level of SK3 activity which is measured at step (i) with the level of SK3 activity which is measured when step (i) is performed in the absence of said candidate compound,
wherein a decrease of SK3 activity in the presence of the candidate compound indicates that the candidate consists of an anti-metastatic compound.

As intended herein, a "functional SK3" is a small conductance $Ca^{2+}$-activated potassium channel expressed on a cell surface under the form of a homo or heteromeric assembly of subunits including at least one polypeptide SK3, which promotes the migration of cells on which said channel is present by (i) increasing $K^+$ efflux from said cells and (ii) increasing the intracellular $Ca^{2+}$ concentration in said cells.

For example, K+ efflux can be measured by patch-clamp experiments and intracellular $Ca^{2+}$ concentration by spectrofluorimetry experiments as described below and in the examples.

More precisely, by "cell expressing a functional SK3" it is intended herein a cell having the two following cumulative properties:
The cell is able to migrate.
The migration of the cell is partially or completely inhibited by a SK3 blocker.

Concerning the first property, cell migration assays are disclosed in more details below, and in the examples. Concerning the second property, SK3 blocker can be selected for example in the group consisting of apamin, with disulfide bonds between Cys1-Cys11 and Cys3-Cys15), 4-aminopyridine (4-AP) and tetraethylammonium (TEA). Preferably, a SK3 blocker is Apamin.

Anti-metastatic compounds are compounds that decrease or block SK3 activity. Anti-metastatic compounds comprise, and preferably consists of compounds able to decrease, block, or prevent metastasis originating from a primary cancer.

By SK3, it is intended herein a polypeptide having at least 90% homology with one of the polypeptides listed in Table 1 below

| Protein Name | Sequence | Gene | Variant | Gene Accession Number |
|---|---|---|---|---|
| hSK3; or SKCa3; or KCa2.3; or SK3 | SEQ ID N° 1 | KCNN3 | variant 1 | AJ251016.1 |
| SK3-1B; SKCa3-1B | SEQ ID N° 2 | KCNN3 | variant 1B | AY138900.1 |
| SK3-1C; SKCa3-1C | SEQ ID N° 3 | KCNN3 | variant 2 | BC042147.1 |
| hSK3_ex4 | SEQ ID N° 4 | KCNN3 | variant with 15aa insertion* | None |

*Wittekindt et al., An Apamin- and Scyllatoxin-Insensitive Isoform of the Human SK3 Channel, Mol Pharmacol 65: 788-801, 2004.

As used herein, "SK3" encompasses the polypeptides comprising, or consisting of an amino acid of sequence selected from the group consisting of sequences SEQ ID No. 1, SEQ ID No. 2, SEQ ID No. 3, and SEQ ID No. 4. Accordingly, "SK3" is a polypeptide or protein.

The polypeptide SK3 used in the examples is the polypeptide SK3 of sequence SEQ ID No. 1.

To determine the percentage of identity between two amino acid sequences, the two sequences are aligned for optimal comparison purposes. For example, gaps can be introduced in one or both of a first and a second amino acid sequence for optimal alignment and non-homologous sequences can be disregarded for comparison purposes.

For optimal comparison purposes, the percentage of identity between two amino acid sequences can be achieved with CLUSTAL W (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)= <<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none>>; (12)

MATRIX=<<default>>; (13) GAP OPEN=<<default>>; (14) END GAPS=<<default>>; (15) GAP EXTENSION=<<default>>; (16) GAP DISTANCES=<<default>>; (17) TREE TYPE=<<cladogram>> et (18) TREE GRAP DISTANCES=<<hide>>.

As used herein, SK3 encompasses a polypeptide comprising an amino acid sequence having at least 90% of identity with the polypeptides of sequences SEQ ID No. 1, SEQ ID No. 2, SEQ ID No. 3, and SEQ ID No. 4. According to the invention a first amino acid sequence having at least 90% of identity with a second amino acid sequence, comprises at least 90%, and preferably at least 91%, 92%, 93%, 94%, 95%, 96%, 97%, 98%, 99, 99.3%, 99.6%, or 99.9% of identity in amino acids with said second amino acid sequence.

SK3 Recombinant Expression

For purposes of developing screening assays designed to identify compounds or compositions that modulate SK3 activity it may be necessary to recombinantly express the SK3 protein, so as to provide cells able to express SK3, with which, the method according to the invention will be performed.

SK3 may be isolated using a variety of different methods known to those skilled in the art. For example, a cDNA library constructed using RNA from a tissue or cell lines expressing SK3 can be screened using a labeled SK3 nucleic acid. Alternatively, a genomic library may be screened to obtain nucleic acids encoding SK3. Further, nucleic acid sequences encoding SK3 may be obtained by performing a polymerase chain reaction (PCR) using two oligonucleotide primers designed on the basis of the known nucleotide sequences encoding SK3. The template for the reaction may be cDNA obtained by reverse transcription of mRNA prepared from cell lines or tissue expressing SK3.

SK3, mutated, truncated or deleted forms of SK3, SK3 fusion proteins, or polypeptide comprising SK3 can be prepared for a variety of uses, including but not limited to, the generation of antibodies, and the screening for compounds that can be used to modulate SK3 activity.

SK3 fusion proteins include fusions to an enzyme, fluorescent protein, a polypeptide tag or luminescent protein which provide a marker function.

While SK3 can be chemically synthesized using standard techniques (e.g., see Creighton, 1983, Proteins: Structures and Molecular Principles, W.H. Freeman & Co., N.Y.), SK3 may be advantageously produced by recombinant DNA technology using techniques well known in the art for expressing a nucleic acid containing SK3 gene sequences and/or coding sequences. Such methods can be used to construct expression vectors containing the SK3 nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, Molecular Cloning. A Laboratory Manual, Second Edition, Cold Spring Harbor Press, N.Y.; and Ausubel et al., 1989, Current Protocols in Molecular Biology, Green Publishing Associates and Wiley Interscience, N.Y.).

A variety of host-expression vector systems may be utilized to express the SK3 nucleotide sequences. Where a SK3 derived peptide or polypeptide is expressed as a soluble derivative (e.g., peptides corresponding to the extracellular, transmembrane or cytoplasmic domain) and is not secreted, the peptide or polypeptide can be recovered from the host cell. Alternatively, where the SK3 peptide or polypeptide is secreted the peptide or polypeptide may be recovered from the culture media. However, the expression systems also include engineered host cells that express SK3 or functional equivalents, anchored in the cell membrane. Purification or enrichment of the SK3 from such expression systems can be accomplished using appropriate detergents and lipid micelles and methods well known to those skilled in the art. Such engineered host cells themselves may be used in situations where it is important not only to retain the structural and functional characteristics of the SK3, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing SK3 nucleotide sequences; yeast transformed with recombinant yeast expression vectors containing SK3 nucleotide sequences or mammalian cell systems or insect cell systems harboring recombinant expression constructs containing promoters derived from the genome of mammalian or insect cells or from mammalian or insect viruses.

Appropriate expression systems can be chosen to ensure that the correct modification, processing and sub-cellular localization of the SK3 protein occurs. To this end, eukaryotic host cells, which possess the ability to properly modify and process the SK3 protein, are preferred. For long-term, high yield production of recombinant SK3 protein, such as that desired for development of cell lines for screening purposes, stable expression is preferred. Rather than using expression vectors which contain origins of replication, host cells can be transformed with DNA controlled by appropriate expression control elements and a selectable marker gene. Following the introduction of the foreign DNA, engineered cells may be allowed to grow for 1-2 days in enriched media, and then switched to a selective media. Such engineered cell lines may be particularly useful in the screening method according to the invention, where an evaluation of compounds that modulate the endogenous activity of the SK3 gene product is sought.

Cells that endogenously express SK3 can be used in the method of screening according to the invention. Such cells include, for example, MDA-MB435-S. Alternatively, cell lines, such as MCF-7, 184A1, 293T, NIH-3T3, and the like, genetically engineered to express SK3 can be used for screening purposes. Preferably, host cells genetically engineered to express a functional SK3 are those capable of signal transduction in response to contact with growth factors such as FGF-2. Further, ooyctes or liposomes engineered to express the SK3 protein may be used in assays developed to identify modulators, and preferably inhibitors of SK3 activity.

SK3 Activity Measurement

The ability of a test compound to modulate SK3 activity may be assayed using a variety of different methods. Preferably, in the method of screening according to the invention, the activity of SK3 is measured using a cell migration assay.

As disclosed in the examples, cell migration can be measured as described in Roger S, Potier M, Vandier C, Le Guennec J Y, Besson P. "Description and role in proliferation of iberiotoxin-sensitive currents in different human mammary epithelial normal and cancerous cells. Biochim Biophys Acta 2004; 1667:190-9."

Thus, according to the invention, a cell migration assay comprises the following steps:
bringing into contact cells expressing SK3 with a membrane possessing pores sufficiently large to allow for the cells to pass through,
quantifying the cells that pass through the membrane.

In the test above, a quantity of cells passing through the membrane, higher in a first sample of cells than in a second one, indicates a level of SK3 activity higher in the first sample than in the second one.

Similarly, a quantity of cells passing through the membrane, lower in the presence of a candidate compound, in comparison to the quantity measured in the absence of the candidate compound, indicates that the candidate consists of an anti-metastatic compound.

Cell migration can be measured similarly through Matrigel-coated filters as described in Albini et al., (Albini A et al., 1987, Cancer Res 47:3239-3245). The level of cell migration and invasion through Matrigel-coated filters is measured in the presence of a test compound and compared to the level of cell migration and invasion observed in the absence of a test compound. A decrease in the level of cell migration and invasion in the presence of a test compound indicates identification of an inhibitor of SK3 activity and an increase in the level of cell migration and invasion in the presence of a test compound indicates identification of an activator of SK3 activity.

It has been shown, according to the invention that, SK3 activity is linked to an increased $K^+$ efflux, which is reduced by SK3 inhibitors.

Consequently, according to another embodiment of the invention, the activity of SK3 is measured by detecting the level of K+ efflux from the cell expressing SK3.

The level of K+ efflux can be measured by patch-clamp experiments, well known from the man skilled in the art and described in Example 1.

According to the invention, detecting the level of K+ efflux, comprises the step of:
Bringing into contact the membrane of a cell expressing SK3 with a patch clamp electrode,
measuring K+ current by using said electrode.

In the test above, a K+ current, higher in a first sample of cells than in a second one, indicates a level of SK3 activity higher in the first sample than in the second one.

Illustratively, a $K^+$ current, lower in the presence of a candidate compound, in comparison to the $K^+$ current measured in the absence of the candidate compound, indicates that the candidate compound consists of an anti-metastatic compound.

Alternatively, the activity of SK3 is measured by detecting the intracellular $Ca^{2+}$ level in the cell expressing SK3. An intracellular concentration of $Ca^{2+}$, higher in a first sample of cells than in a second one, indicates a level of SK3 activity higher in the first sample than in the second one.

As disclosed in the examples, intracellular $Ca^{2+}$ level can be measured as described in Roger S, Potier M, Vandier C, Le Guennec J Y, Besson P. "Description and role in proliferation of iberiotoxin-sensitive currents in different human mammary epithelial normal and cancerous cells. Biochim Biophys Acta 2004; 1667:190-9."

According to a preferred embodiment of the invention the activity of SK3 is measured by detecting the level of SK3 expression, for example by using an antibody directed to SK3.

By "level of SK3 expression", it is intended herein, the level of SK3 transcription or translation. For example, The SK3 transcription level can be obtained by measuring the SK3 mRNA level.

According to the invention, detecting the level of SK3 expression, comprises the step of:
Bringing into contact a cell expressing SK3 with an antibody directed against SK3,
detecting the binding of said antibody to SK3.

In the test above, a level of SK3 expression, higher in a first sample of cells than in a second one, indicates a level of SK3 activity higher in the first sample than in the second one.

The detection of the binding of SK3 antibody to SK3 can be achieved using a labelled antibody, as described below, in the part "Diagnostic methods".

In order to measure SK3 activity, one or several methods above can be used, in combination, or separately.

In a particular embodiment of the invention, the method of screening according to the invention comprises a preliminary step, before step (i) comprising:
(a) incubating a candidate compound to be tested with SK3, and
(b) assaying for the binding of the candidate compound to be tested with SK3, and
(c) selecting positively a candidate compound for step (i) if said candidate compound binds to SK3.

Non-cell based assay systems may be used to identify compounds that interact with SK3 directly or indirectly and regulate the activity of SK3. Recombinant SK3, including peptides corresponding to different functional domains, or SK3 fusion proteins, may be expressed and used in assays to identify compounds that interact with SK3.

The candidate compounds, which may be screened according to the screening method above, may be of any kind, including, without being limited to, natural or synthetic compounds or molecules of biological origin such as polypeptides.

Recombinantly expressed SK3 or fusion proteins containing one or more of the SK3 functional domains may be prepared as described above, and used in the non-cell based screening assays. For example, SK3, or a soluble truncated SK3, e.g., in which the one or more of the cytoplasmic and transmembrane domains is deleted from the molecule, a peptide corresponding to the extracellular domain, or a fusion protein containing the SK3 extracellular domain fused to a protein or polypeptide that affords advantages in the assay system (e.g., labeling, isolation of the resulting complex, etc.) can be used.

Where compounds that interact with the cytoplasmic domain are sought to be identified, peptides corresponding to the SK3 cytoplasmic domain and fusion proteins containing the SK3 cytoplasmic domain can be used.

The SK3 protein may also be one which has been fully or partially isolated from cell membranes, or which may be present as part of a crude or semi-purified extract. As a non-limiting example, the SK3 protein may be present in a preparation of cell membranes.

The binding of the candidate compound to SK3 can be carried on by the one skilled in the art, for example by using a Two-hybrid system. Other means, known from the one skilled in the art can be used for the binding assays such as the use of bio sensor techniques (Edwards and Leatherbarrow (1997) or also by Szabo et al. (1995)), affinity chromatography, or High Throughput Screening (HTS), (Leblanc et al 2002).

Preferably, step (b) consists of subjecting to a gel migration assay the mixture obtained at the end of step (a) and detecting the complexes formed between the candidate compound and SK3.

The gel migration assay can be carried out as known by the one skilled in the art.

The detection of the complexes formed between the candidate compound and SK3 can be easily observed by determining the stain position (protein bands) corresponding to the proteins analysed since the apparent molecular weight of a protein changes if it is part of a complex with another protein.

On one hand, the stains (protein bands) corresponding to the proteins submitted to the gel migration assay can be detected by specific antibodies for example antibodies specifically directed against SK3. On the other hand, SK3 can be tagged for an easier detection of the protein/candidate compound on the gel. For example, SK3 can be fused to GST, HA, a poly-Histidine chain, or other detectable molecules in order to facilitate the identification of the different proteins on the gel.

One aim of the method of screening above is to provide compounds that can be used for treating cancer, and more particularly, to provide compounds for preventing individuals with a cancer from the occurrence of metastasis or to reduce further metastasis.

Metastasis involves, in addition to migration, the capacity of tumor cells to form dynamic adhesive interactions with different host cell surfaces.

Accordingly, in order to select compounds which will be very active against the occurrence of metastasis, the methods of screening above can comprise the following additional step:
measuring cellular aggregation and/or adhesion of cells to endothelium in the presence or absence of the test compound, and
selecting positively the tested compound if cellular aggregation or adhesion of cells to endothelium is lower in the presence of the test compound.

For example, coaggregation assays may be used to measure the ability of a test compound to modulate cellular aggregation. In such assays, single cell suspensions of cells expressing SK3 are mixed in the presence and absence of the test compound. The mixed cells are then observed to determine whether cell aggregation has occurred. In a specific embodiment of the invention, the cells may be labeled with a fluorescent dye prior to mixing, to facilitate visualization of aggregating cells.

The level of cell aggregation is measured in the presence of a test compound and compared to the level of cell aggregation observed in the absence of a test compound.

According to the invention, an anti-metastatic compound, is preferably a compound able to decrease the level of cell aggregation.

The ability of a test compound to modulate adhesion of cells to endothelium may be measured as follows. For example, human endothelium monolayers may be formed by plating HUVEC cells on gelatin coated cover slips. Cells expressing SK3 are then added to the endothelium monolayers and incubated for a time sufficient to allow adhesion to the monolayer. The level of cell adhesion is measured in the presence of a test compound and compared to the level of adhesion observed in the absence of a test compound.

According to the invention, an anti-metastatic compound is preferably a compound able to decrease the level of cell adhesion.

In a particular embodiment of the invention, the method of screening according to the invention comprises a preliminary step, before step (i) comprising:
(a) incubating a candidate compound to be tested with SK3,
(b) assaying for the binding of the candidate compound to be tested with SK3.

Methods of Detection According to the Invention

As already mentioned above, there is a relevant correlation between the level of SK3 expression and the ability of cells to migrate and by the way, to develop metastatic cancers in a patient.

Accordingly, an object of the invention is a method for determining in vitro the presence or absence of a metastatic cancer in a subject, comprising the steps of:
(i) quantifying SK3 activity in a test sample comprising cancerous cells of a specific tissue type obtained from a cancerous subject,
(ii) comparing the level of SK3 activity which is quantified at step (i) with the level of SK3 activity which is quantified when step (i) is performed in a control sample comprising non-cancerous cells or non-metastatic cancerous cells of the same tissue type,
wherein a greater level of SK3 activity in the test sample, compared to the control sample, indicates the presence of a metastatic cancer in the cancerous subject, and a level of SK3 activity in the test sample identical to, or lower than the level of SK3 activity quantified in the control sample, indicates the absence of a metastatic cancer in the cancerous subject.

In most human malignancies, distant metastases are often too small to be detected at the time the primary tumor is treated. Furthermore, widespread initiation of metastatic colonies usually occurs before clinical symptoms of metastatic disease are evident.

Consequently, the method above is particularly useful for detecting metastatic cancers, i.e. secondary tumors colonies originating from a primary tumor, in an early state.

It is to be noted, however, that the presence or absence of all types of metastatic cancer cannot be detected by the method above. Indeed, there exists for example some cancer cell lines with highly metastazing properties, which does not express SK3. Among them, T47D cells or MCF7 can be cited.

By definition, the cells making part of the samples described above, i.e. cancerous cells, non cancerous cells, and non-metastatic cancerous cells are cells of a specific tissue type.

According to the invention, the specific tissue type of the cells is for example endothelial, ectodermic, mesenchymatic, muscular, or endocrine.

As used herein, cancerous cells designates cells possessing characteristics typical of cancer-causing cells, such as uncontrolled proliferation, immortality, metastatic potential, rapid growth and proliferation rate, and certain specific morphological features. Cancerous cells are often in the form of a tumour, but such cells may exist alone within the body, or may be non-tumorigen cancer cells, such as a leukaemia cell. Cancerous cells can be associated with many kinds of cancers including, but not limited to apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, coat cell, papillary, scirrhous, bronchiolar, bronchogenic, squamous cell, and transitional cell), histiocytic disorders, leukaemia (e.g. B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumours, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chondroma, cranio-pharyngioma, dysgerminoma, hamartoma, mesenchymoma, mesonephroma, myosarcoma, ameloblastoma, cementoma, odontoma, teratoma, thymoma, trophoblastic tumour, adenocarcinoma, carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyl lodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g. Ewing, experimental, Kaposi, and mast cell), neoplasms (e.g. bone, breast, digestive system, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. The invention could be used in combination with other treatment modalities, such as chemotherapy, cryotherapy, hyperthernia, radiation therapy, and the like.

Preferably, the cells of a specific tissue type, used in the method above are ectodermic cells for example originating from a melanoma, or epithelial cells, for example originating from a breast cancer The invention also relates to a method for the in vitro assessment of the progression of the metastatic property of a cancer in a subject, wherein said method comprises the steps of:
(i) quantifying SK3 activity in a sample comprising cancerous cells of a specific tissue type obtained from a cancerous subject, at a first time point,
(ii) quantifying SK3 activity in a sample comprising cancerous cells of the same tissue type, obtained from said cancerous subject, at a subsequent time point,
wherein a greater level of SK3 activity at step (ii), compared to step (i), indicates an increase in the metastatic property of the cancer from the subject, and a lower level of SK3 activity at step (ii), compared to step (i), indicates a decrease in the metastatic property of the cancer from the subject.

As used herein, the "assessment of the progression" of a cancer consists of data indicative of the increase or decrease in the level of SK3 activity in a patient with a cancer, during time, since, as already mentioned above, there is a relevant correlation between the level of SK3 activity and the ability of cancerous cells to migrate and by the way, to develop metastasis from a primary cancer.

Compounds According to the Invention that Inhibits SK3 Activity

The present invention provides for compounds capable of modulating the activity of SK3 and/or the expression of SK3 thereby regulating the migratory activity of cells.

Compounds that modulate SK3 activity can be identified with the method of screening described above. For example, compounds that affect SK3 activity include but are not limited to compounds that bind to SK3, and reduce SK3 activity. Compounds that may be identified can do not bind directly to SK3 but being able to alter SK3 activity by altering the activity of a protein that interacts with SK3.

The compounds which may be screened in accordance with the invention include, but are not limited to, small organic or inorganic compounds, peptides, antibodies and fragments thereof, and other organic compounds.

Peptides are, for example, soluble peptides, identified from random peptide libraries (see, e.g., Lam K S et al., 1991, Nature 354:82-84; Houghten R et al., 1991, Nature 354:84-86); or combinatorial chemistry-derived molecular library made of D- and/or L-configuration amino acids, phosphopeptides including, but not limited to, members of random or partially degenerate, directed phosphopeptide libraries; (see, e.g., Songyang Z et al., 1993, Cell 72:767-778), antibodies including, but not limited to, polyclonal, monoclonal, humanized, anti-idiotypic, chimeric or single chain antibodies, and FAb, F(ab').sub.2 and FAb expression library fragments, and epitope binding fragments thereof, and small organic or inorganic molecules.

Accordingly, candidate compounds may be selected from the group consisting of (a) proteins or peptides, (b) nucleic acids, and (c) organic or mineral chemical compounds.

Candidate compounds consisting of nucleic acids, comprise a sequence that specifically binds to SK3. Sequence of said nucleic acids may consist of an aptamer, preferably selected in libraries of pre-selected candidate nucleic acids by the SELEX method, well known of the one skilled in the art. For performing the SELEX method, the one skilled in the art may refer to the content of the U.S. Pat. No. 5,475,096 and U.S. Pat. No. 5,270,163, the content of these two documents being herein incorporated by reference.

It has been shown according to the invention that antibodies directed against SK3 can acts as SK3 inhibitors.

Accordingly, the invention concerns also antibodies directed against SK3. These antibodies include, polyclonal, monoclonal, humanized, anti-idiotypic, chimeric or single chain antibodies, and FAb, F(ab').sub.2 and FAb expression library fragments, and epitope binding fragments thereof.

These antibodies can be directed against all or part of SK3, and for example, against the extracellular, transmembrane or cytoplasmic domain of SK3.

The invention concerns further, a pharmaceutical composition comprising an antibody directed against SK3, in combination with at least one physiologically acceptable excipient.

Accordingly, the invention is also directed to the use of an antibody directed against SK3, for the manufacture of a pharmaceutical composition for preventing or treating the occurrence of metastasis from a primary cancer.

Polynucleotides

In an embodiment of the invention, the level of SK3 expression can be modulated using antisense approaches to inhibit or prevent translation of SK3 mRNA transcripts or triple helix approaches to inhibit transcription of the SK3 gene.

Antisense approaches involve the design of oligonucleotides either DNA or RNA, designated siRNA that are complementary to SK3 mRNA. The antisense oligonucleotides bind to the complementary mRNA transcripts and prevent translation. Absolute complementarity, although preferred, is not required. One skilled in the art can ascertain a tolerable degree of mismatch by use of standard procedures to determine the melting point of the hybridized complex. Such nucleotides have been prepared according to the invention.

Two sets of SK3 specific siRNA have been designed:
a first set, targeted against SK3 exon 1 comprises a sense polynucleotide 5'-GAAAGCGACUGAGUGAC-UAdTdT-3' corresponding to sequence SEQ ID No. 5 and an anti-sense sense polynucleotide 5'-UAGU-CACUCAGUCGCUUCdTdT-3', corresponding to sequence SEQ ID No. 6, both located in exon 1;
a second set, targeted against SK3 exon 3 comprises a sense polynucleotide 5'-CCAUUCCUGGCGAGUA-CAAdTdT-3' corresponding to sequence SEQ ID No. 7 and an anti-sense sense polynucleotide 5'-UU-GUACUCGCCAGGAAUGGdTdT-3', corresponding to sequence SEQ ID No. 8, both located in exon 3.

Accordingly, the invention concerns (i) a set of nucleic acids of sequence SEQ ID No. 5, and SEQ ID No. 6, and a set of nucleic acids of sequence SEQ ID No. 7 and SEQ ID No. 8.

As shown in the examples herein, these sets of polynucleotides can be transfected into cells in order to reduce SK3 expression, and by the way, cell migration.

In another embodiment of the invention, ribozyme molecules designed to catalytically cleave SK3 mRNA transcripts can also be used to prevent translation of SK3 mRNA and expression of SK3.

Alternatively, endogenous SK3 gene expression can be reduced by targeting deoxyribonucleotide sequences complementary to the regulatory region of the SK3 gene (i.e., the SK3 promoter and or enhancers) to form triple helical structures that prevent transcription of the SK3 gene in targeted cancer cells in the body.

The nucleotides of the invention, i.e., antisense, ribozyme and triple helix forming oligonucleotides, may be synthesized by standard methods known in the art, e.g., by use of an automated DNA synthesizer Alternatively, recombinant expression vectors may be constructed to direct the expression of the oligonucleotides of the invention. Such vectors can be constructed by recombinant DNA technology methods standard in the art. In a specific embodiment, vectors such as viral vectors may be designed for gene therapy applications where the goal is in vivo expression of inhibitory oligonucleotides in targeted cells.

Use of the Compounds According to the Invention.

The compounds described above are capable of modulating the activity of SK3 and/or the expression of SK3 thereby regulating the migratory activity of cells.

Accordingly, the invention is also directed to the use of an antibody directed against SK3, for the manufacture of a pharmaceutical composition for preventing or treating the occurrence of metastasis from a primary cancer.

The invention also relates to the use of
a set of polynucleotides of sequence SEQ ID No. 5, and SEQ ID No. 6, or,
a set of polynucleotides of sequence SEQ ID No. 7, and SEQ ID No. 8,
for manufacturing a pharmaceutical composition for treating a cancer, and preferably a metastatic cancer.

The compounds according to the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing SK3 are exposed to or otherwise administered a therapeutic compound and the effect of such a therapeutic upon SK3 activity is observed. In a specific embodiment of the invention the ability of a compound to inhibit cell migration, may be assayed.

Pharmaceutical Compositions According to the Invention

The present invention provides for compositions comprising an effective amount of a compound capable of modulating the activity of SK3, or the expression of SK3, thereby regulating the migratory activity of cells, and a pharmaceutically acceptable carrier.

Suitable carriers and their formulations are described in Remington's Pharmaceutical Science, 16$^{th}$ ed, 1980, Mack publishing Co, edited by Oslo et al.

By <<physiologically acceptable carrier>> is meant solid or liquid filler, diluent or substance, which may be safely used in systemic or topical administration. Depending on the particular route of administration, a variety of pharmaceutically acceptable carriers well known in the art include solid or liquid fillers, diluents, hydrotopes, surface active agents, and encapsulating substances.

These compositions will typically contain an effective amount of a SK3 inhibitor, together with a suitable amount of carrier to prepare pharmaceutically acceptable compositions suitable for effective administration to the patient.

An "effective amount" of the SK3 inhibitor, is an amount that decreases cell migration, and/or that is associated with a detectable decrease in SK3 activity as measured by one of the above assays.

The pharmaceutical composition according to the invention may be administered parenterally or by other methods that ensure its delivery to the bloodstream in an effective form. Dosages and desired drug concentrations of such pharmaceutical compositions may vary depending on the particular use envisioned.

Sterility is readily accomplished by sterile filtration through (0.2 micron) membranes.

The pharmaceutical composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The amount of the SK3 inhibitor to be administered will be governed by such considerations, and is the minimum amount necessary to induce a decrease in SK3 activity in a patient or a mammal.

The amount of the SK3 inhibitor to be administered will vary from 0.01 mg/kg to 100 mg/kg, preferably from 0.01 mg/kg to 50 mg/kg, and most preferably 0.05 mg/kg to 25 mg/kg, and for example 10 mg/kg.

Such amount is preferably below the amount that is toxic to the mammal.

Diagnostic Methods According to the Invention

In accordance with the invention, measurement of SK3 activity can be used for the diagnosis of diseases such as cancer. Moreover, the monitoring of SK3 levels can be used prognostically to state the progression of the disease or the efficacy of drug treatment. The detection of SK3 levels in a sample from a patient can be accomplished by any of a number of methods. Such methods include immunoassays which include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, and flow cytometry techniques.

Such an immunoassay is carried out by a method comprising contacting a sample derived from a subject with an antibody immunoreactive with SK3 under conditions such that specific antigen-antibody binding can occur, and detecting or measuring the amount of any immunospecific binding to SK3. In a specific aspect, such binding of antibody to samples, for example, can be used to detect the presence of SK3 wherein the detection of SK3 is an indication of a diseased condition. i.e., the presence of cancer cells with an increased metastatic potential. The levels of SK3 in a sample are compared to the levels present in an analogous sample from a subject not having the disorder.

These samples are samples of cell of a specific tissue type, as defined above.

Antibodies can be used in assays, such as the immunoassays listed above, to detect, prognose, diagnose, or monitor cancer in an individual, or monitor the treatment thereof. In particular, such an immunoassay is carried out by a method comprising contacting a sample derived from a subject with an antibody under conditions such that immunospecific binding can occur, and detecting or measuring the amount of any immunospecific binding by the antibody. In addition, reagents other than antibodies, such as, for example, nucleic acid molecules, polypeptides or chemical compounds that specifically bind to SK3, can be used in assays to detect the expression of SK3.

In a specific aspect, such binding of antibody to biological samples, can be used to detect expression of the protein wherein the expression of the protein is an indication of a diseased condition. The levels of expressed proteins are compared to levels present in an analogous sample from a portion of the body or from a subject not having the disorder.

In another specific aspect, flow cytometry can be used to detect expression of SK3 in a cell. Indeed, SK3 can be detected for example in a sample of cancerous cells, by using an anti-SK3 antibody. Such a technique can be carried out for example according to: Chassevent et al., S-phase fraction and DNA ploidy in 633 T1T2 breast cancers: a standardized flow cytometric study. Clin Cancer Res. 2001 April; 7(4):909-17.

Methods of Treatment According to the Invention

The present invention provides for methods for the prevention, or the treatment of a cancer, comprising contacting a cell with an effective amount of a SK3 inhibitor, such as disclosed above.

An "effective amount" of the SK3 inhibitor, is an amount that decreases cell migration, and/or that is associated with a detectable decrease in SK3 activity as measured by one of the above assays.

The present invention further provides methods for preventing metastasis from a primary cancer, or for treating metastasis, comprising administering to the subject, a compound as described above, that inhibits SK3. The composition may comprise an amount of SK3 activity inhibitor or modulator of SK3 expression.

The invention provides for treatment or prevention of various diseases and disorders associated with cell migration by administration of a compound that regulates the expression or activity of SK3.

In a non-limiting embodiment of the invention, disorders associated with increased cell migration, and/or metastatic potential are treated or prevented by administration of a compound that inhibits SK3 activity. Such disorders include but are not limited to cancers, including but not limited to, breast cancers, and melanomas.

The invention provides methods of treatment and/or prophylaxis by administration to a subject of an effective amount of a compound of the invention. In a preferred aspect, the compound is substantially purified. The subject is preferably an animal, and is preferably a mammal, and most preferably human.

Various delivery systems are known and can be used to administer a compound capable of regulating SK3 activity, or SK3 expression, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

EXAMPLES

Material and Methods Used in the Examples

Cell Culture

The human mammary cancer cell lines MDA-MB-435s, MDA-MB-231, MCF-7, T47D and SKBR3 were grown in Dulbecco's modified Eagle's medium (DMEM) containing 5% fetal bovine serum (FBS) as already described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667:190-9.). The immortalized normal mammary epithelial cell lines MCF-10A and 184A1 were cultured in DMEM/Ham's F-12, 1:1 mix containing 5% horse serum (Invitrogen Life Technologies, France), insulin (10 µg/ml), epidermal growth factor (20 ng/ml), hydrocortisone (0.5 µg/ml) and, respectively for MCF-10A and 184A1, 100 ng/ml cholera toxin and 1 ng/ml cholera toxin plus 5 µg/ml transferrin. High $K^+$ medium was custom made from $K^+$-, $Na^+$- and $Ca^{2+}$-free DMEM-based medium (Cambrex Bio Science, France) and supplemented at time of use at 60 mM KCl, 84 mM NaCl, 2 mM $CaCl_2$.

All cell lines were obtained from the American Type Culture Collection (ATCC, LGC Promochem, Molsheim, France).

Breast Tissue Samples

Tissue samples were provided from patients treated by surgery in the University Hospital of Tours, in 1991. Tumor and non-tumor tissue samples were selected by a pathologist from fresh specimens and directly frozen in liquid nitrogen until analysis. After thawing of tumors, imprints were done, stained with May-Grunwald-Giemsa and observed by the pathologist to verify for the presence of malignant cells. Control tissue samples were chosen among patients with aneuploid tumors and analyzed by flow cytometry to verify the absence of aneuploid tumor cells.

Cell Proliferation and Cell Migration In Vitro.

Cell proliferation was determined using the tetrazolium salt reduction method, as described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667:190-9.). Cells were seeded on 24-well plates and grown for 48 h. Drugs were then added for 24 h at concentrations that had no effect on cell proliferation. Cell migration was analyzed in 24-well plates receiving 8-µm pore size polyethylene terephtalate membrane cell culture inserts (Becton Dickinson, France), as described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667:190-9.).
Electrophysiology and Intracellular $Ca^{2+}$ Measurements.

Whole-cell potassium currents and intracellular $Ca^{2+}$ ($[Ca^{2+}]_i$) measurements were recorded as described (Roger S, Potier M, Vandier C, Le Guennec J Y, Besson P. Description and role in proliferation of iberiotoxin-sensitive currents in different human mammary epithelial normal and cancerous cells. (Biochim Biophys Acta 2004; 1667:190-9.). Signals were captured using 1322-A Digidata converter (Axon Instruments, USA) and pClamp 8.1 software (Axon Instruments, USA). The analysis were performed using Clampfit 8.1 and Origin 7.0 softwares (Microcal Software, Northampton, Mass., USA).

RT-PCR and Western Blot.

RT-PCR experiments were performed according standard protocols. The following primers were used: SK-2 5'-primer GACTTGGCAAAGACCCAGAA (SEQ ID No. 9) and 3'-primer CCGCTCAGCATTGTAAGTGA (231 pb) (SEQ ID No. 10) and SK3 5'-primer TGGACACTCAGCTCACCAAG (SEQ ID No. 11) and 3'-primer GTTCCATCTTGACGCTCCTC (174 pb). (SEQ ID No. 12).

The ribosomal gene RNA S14 was chosen as the housekeeping gene using the following PCR primers: 5'-primer GGCAGACCGAGATGAATCCTCA-3' (SEQ ID No. 13) and 3'-primer CAGGTCCAGGGGTCTTGGTCC-3' (SEQ ID No. 14).

For Western blot experiments, proteins were electrotransferred onto polyvinylidene fluoride membranes which were incubated with antibodies directed against SK2 and SK3 proteins (1:1000) followed by incubation with a horseradish peroxidase-conjugated anti-rabbit IgG (1:5000; Tebu-Bio, France). Anti-SK2 directed against amino acids 542-559 and anti-SK3 directed against amino acids 2-21 (Sigma-Aldrich, France) were used for Western blot and immunocytochemical experiments. Anti-Actin directed against amino acids 20-33 (Sigma-Aldrich, France) was used for western blot loading control experiments.

Synthesis and Transfection of Small Interfering RNA Directed Against SK3.

Two SK3 specific siRNA were designed: first set, hSK3-ex1-Sense 5'-GAAAGCGACUGAGUGACUAdTdT-3' (sequence SEQ ID No. 5) and hSK3-ex1-Antisense 5'-UAGUCACUCAGUCGCUUCdTdT-3', (sequence SEQ ID N 06) located in exon 1; second set, hSK3-ex3-Sense 5'-CCAUUCCUGGCGAGUACAAdTdT-3' (sequence SEQ ID No. 7) and hSK3-ex3-Antisense 5'-UUGUACUCGCCAGGAAUGGdTdT-3', (sequence SEQ ID No. 8) located in exon 3. The negative control siRNA (scramble) used had the following sequence 5'-AUAACUGUAUCGAAUGUUAUGAGCC-3' (SEQ ID No. 15). Transfections were performed as previously described (Chajes V, Cambot M, Moreau K, Lenoir G M, Joulin V. Acetyl-CoA carboxylase-alpha is essential to breast cancer cell survival. Cancer Res, in press 2006.).

Transient Transfection of SK3 Protein Channel.

The plasmid containing full-length rat SK3 cDNA (SK3-pTracer-CMV2) and the empty vector (pTracer-CMV2) (generous gifts from Dr. S. Lidofsky, University of Vermont, Burlington, USA) were transfected into MCF-7 and 184A1 cells using lipofectamine 2000 (Invitrogen Life Technologies, France). Transfections were performed according to the manufacturer's protocol.

Immunocytochemistry.

MDA-MB-435s were incubated with anti-SK3 antibody (1:100) followed by Alexa fluor 488 nm goat anti-rabbit (1:1000; Molecular probes). Stained cells were viewed with an Olympus Fluoview 500 Instrument confocal microscope.

Solutions and Drugs.

The physiological saline solution (PSS) in mM: NaCl 140, $MgCl_2$ 1, KCl 4, $CaCl_2$ 2, D-glucose 11.1, and HEPES 10, adjusted to pH 7.4 with NaOH. The pipette solution for the whole-cell recording, pCa=7 was (in mM): K-glutamate 125, KCl 20, $CaCl_2$ 0.37, $MgCl_2$ 1, Mg-ATP 1, EGTA 1, HEPES 10, adjusted to pH 7.2 with KOH. Tetraethylammonium (TEA), 4-aminopyridine (4-AP) and apamin were added to the PSS or culture media at the concentrations indicated in the Figure legends. All drugs and chemicals were purchased from Sigma-Aldrich (St Quentin, France), except Lei-Dab7 which was a generous gift from Dr. J. M. Sabatier, UMR CNRS 6560, Marseille, France.

Statistics.

Unless otherwise indicated, data were expressed as mean±standard error of the mean (n=number of cells). Statistical analysis, performed with StatView 4.57 software (Abacus Concepts, Berkeley, USA) was made using Student t-test or one-way factor ANOVA followed by post hoc Bonferroni-Dunn test. Differences were considered significant when p=0.05.

EXAMPLES

Example 1

Figure 1A:
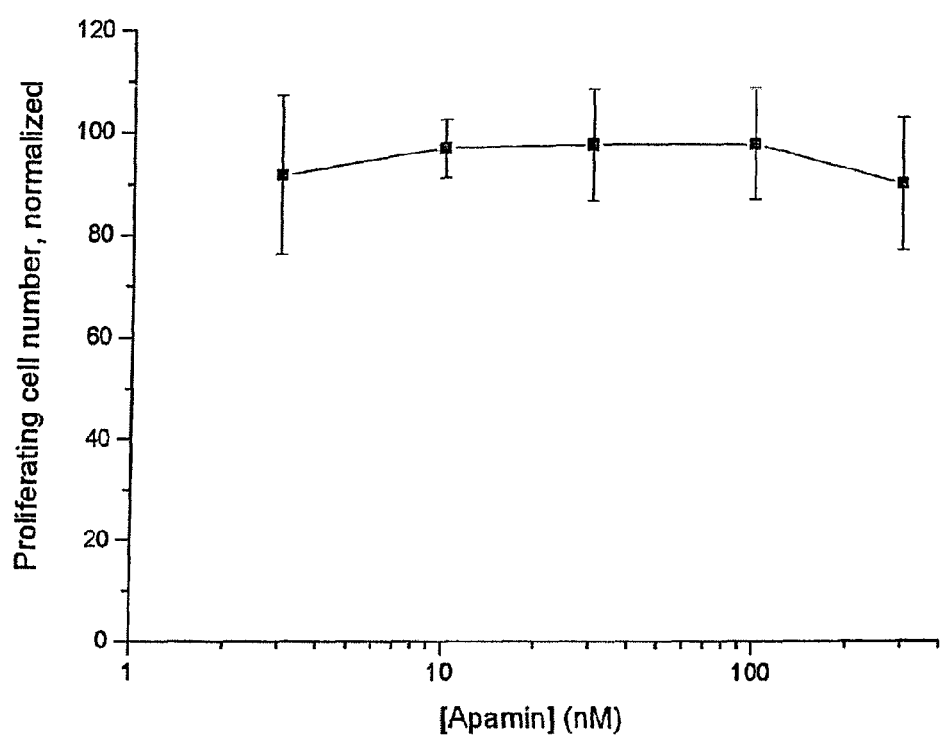
FIG. 1: Involvement of SK channels in MDA-MB-435s cell migration. Histograms showing the inhibitory effect on cell migration of apamin (A), Lei-Dab$^7$, TEA, 4-AP (B) and increasing concentration of external $K^+$ (C). Cells were seeded at 40000 in a cell culture insert in DMEM with 5% FBS±drugs or [$K^+$] 60 mM. The lower compartment of the insert contained DMEM with 10% FBS as a chemoattractant±drugs or [$K^+$] 60 mM. After 24 h, cells of the lower compartment were stained with hematoxylin (A, bottom) and counted. The normalized cell number corresponded to the ratio of total number of migrating cells in presence of drug or [$K^+$] 60 mM/total number of migrating cells in control experiments. The drug concentrations selected have no effect on cell proliferation and viability (example with apamin in A, insert). Scale bar=10 μm for the two panels. Results from two separate experiments performed in triplicate are expressed as mean±S.E.M. * significantly different from control at p<0.05.
Figure 1:
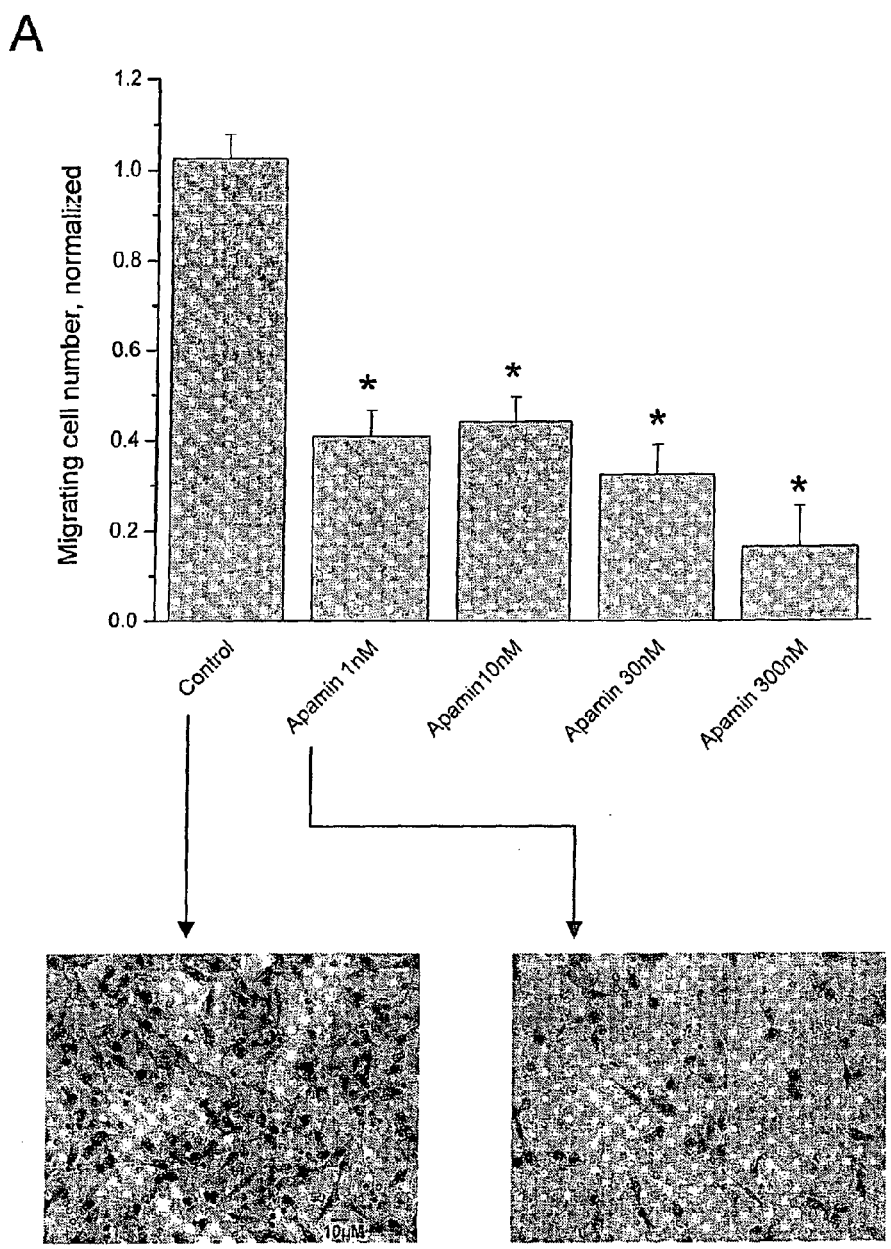
Figure 1:
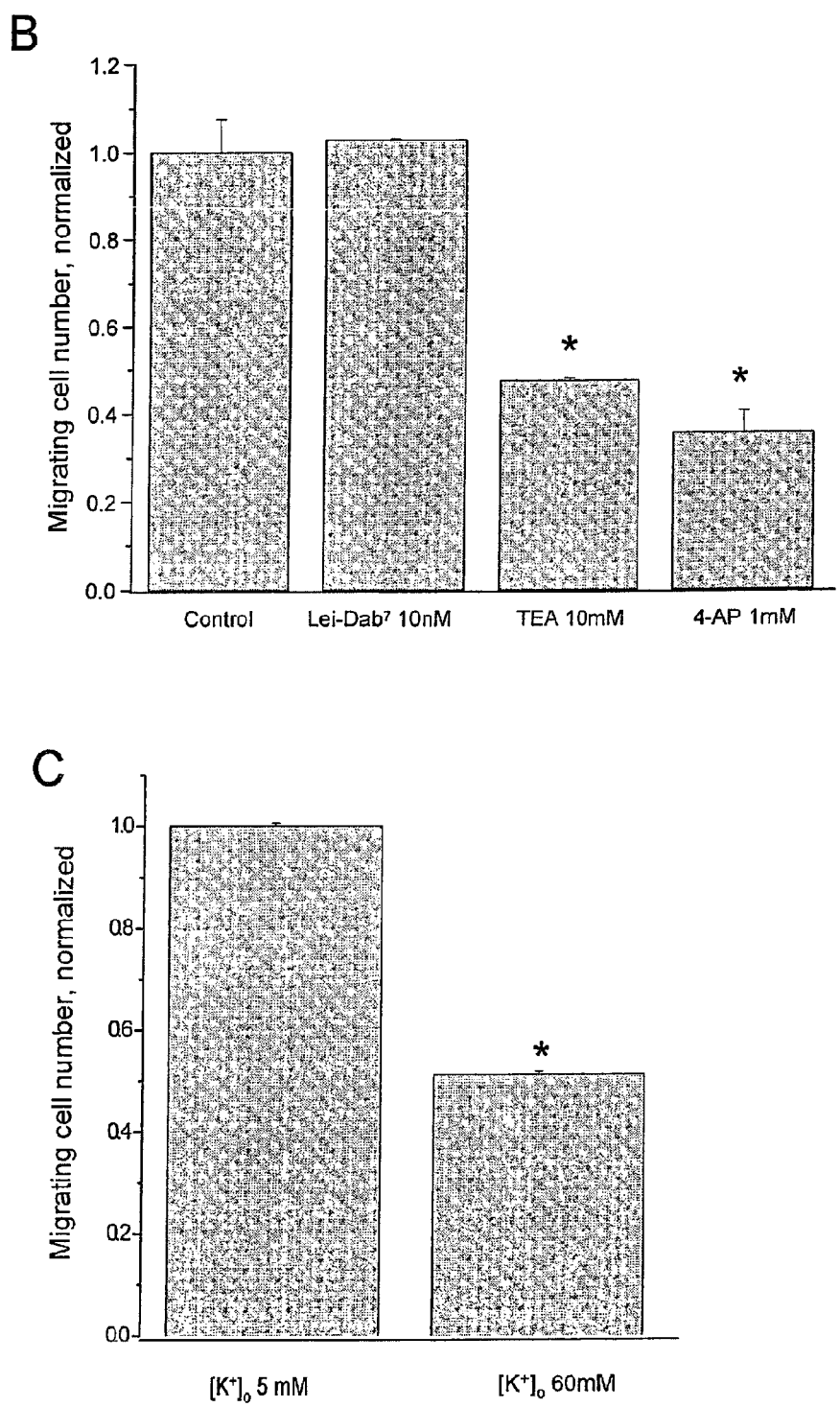

SKCa Channels are Involved in MDA-MB-435s Cell Migration by Regulating Membrane Potential Cell migration, a key mechanism in epithelial tumorigenesis, has been found to be regulated by intracellular $Ca^{2+}$ which depends upon the activity of potassium channels. As a consequence of SK channel activity, it has been speculated that SK channels might be involved in the migratory ability of cancer cells, and the effect of various blockers of SK channels on MDA-MB-435s cell migration have been tested. Apamin blocks SK2 and SK3 channels at low concentration (1 nM), weakly blocks SK1 and does not affect SK4. As shown in FIG. 1A, apamin treatment decreased the number of migrating cells, without affecting cell proliferation/viability. A similar inhibitory effect was found using two general blockers of $K^+$ channels, 4-AP that blocks SK3 channel, and TEA that blocks both SK2 and SK3 channels (FIG. 1B).

In contrast a specific SK2 channel blocker, Lei-Dab7 (Shakkottai V G, Regaya I, Wulff H, et al. Design and characterization of a highly selective peptide inhibitor of the small conductance calcium-activated K+ channel, SkCa2. J Biol Chem 2001; 276:43145-51.), has no effect on MDA-MB-435s cell migration (FIG. 1B). Since no specific SK3 channel blocker is available, it was not possible to prove the involvement of SK3 by this approach.

To verify the modulation of [Ca2+]i by SK channels inhibition, [Ca2+]i has been measured in MDA-MB-435s following 24 h apamin treatment. As expected, 10 nM apamin (a concentration sufficient to block SK2 and SK3 channels) decreased basal [Ca2+] by 46% (from 379±30 nM, n=28, to 204±18 nM, n=34, p<0.05), confirming that apamin-sensitive channels control [Ca2+]i. Moreover, when MDA-MB-435s cells were cultured in the presence of high extracellular K+ (60 mM versus 5 mM in classical DMEM) the number of migrating cells decreased to a level close to that obtained with apamin, TEA and 4-AP (FIG. 1C). Increasing extracellular K+ changes K+ equilibrium potential (EK) from −86 mV to −22 mV (calculated using Nernst equation) and, as a consequence, leads to membrane depolarization.

Figure 2:
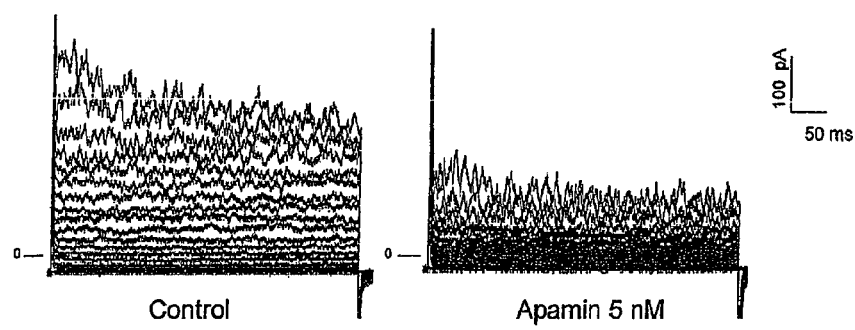
FIG. 2: Regulation of resting membrane potential by SK channels in MDA-MB-435s cells. A—Example of whole-cell macroscopic $K^+$ currents recorded in one cell without (control) or with apamin in the external medium. Currents were generated by stepwise 8 mV depolarizing pulses (400 ms duration; 5 sec intervals) from a constant holding potential of −70 mV up to +58 mV. Signals were filtered at 1 kHz and digitized at 10 kHz.
Figure 2:
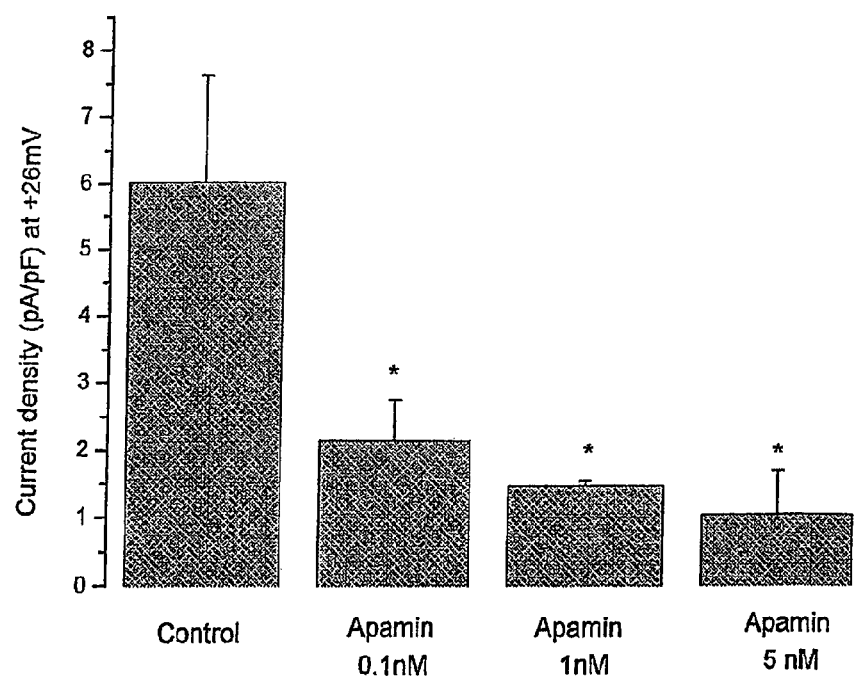
Figure 2:
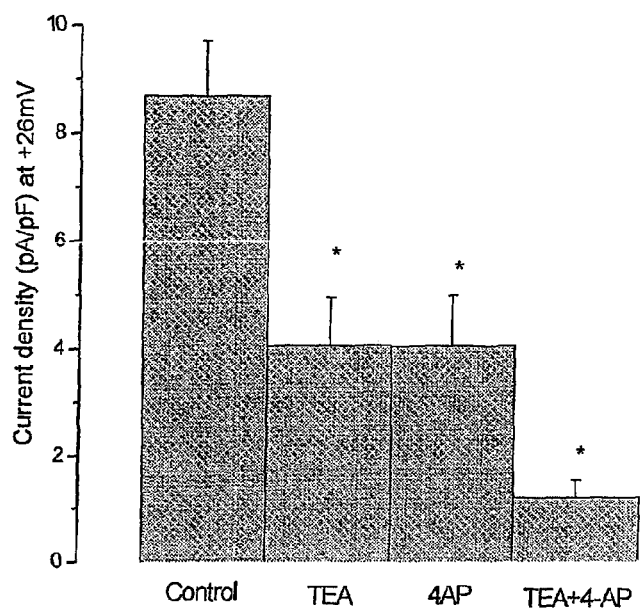
Figure 2:
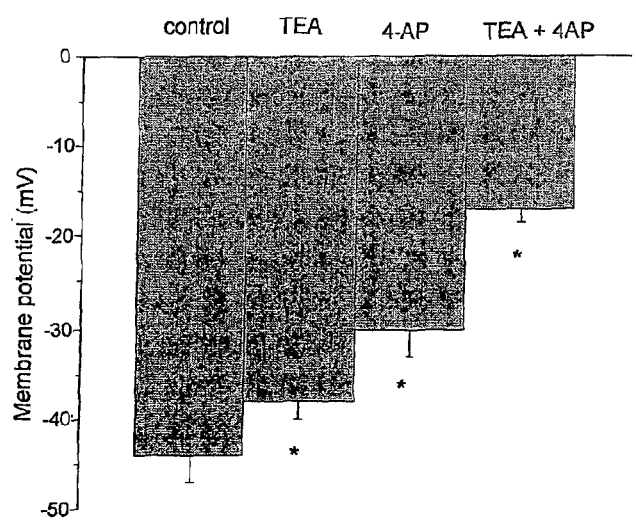

To confirm that SK channels regulate membrane potential of MDA-MB-435s cells, patch-clamp experiments have been performed. FIG. 2A shows typical examples of whole-cell outward currents recorded in MDA-MB-435s cells. These outward currents showed no apparent time-dependence which is one characteristic of all SK currents. To study the possible involvement of SK channels in these epithelial cells, previously described blockers of SK channels have been tested (Apamin, TEA and 4-AP). As illustrated in FIGS. 2A and 2B, apamin largely decreased MDA-MB-435s outward currents. The blocking effect of apamin, which is dose-dependent, started at very low concentration, and estimated IC50 was lower than 0.1 nM (FIG. 2B), suggesting that this apamin-sensitive current could be composed of SK2 or SK3 channels. Similarly, both TEA or 4-AP decreased the outward currents by 50% (FIG. 2C) and depolarized membrane of MDA-MB-435s cells (FIG. 2D). Interestingly, co-treatment with TEA and 4-AP led to an additive effect (FIGS. 2C and 2D), suggesting that those two blockers do not act on the same SK channel sub-types. Finally, SK2 and SK3 channels both regulate membrane potential of MDA-MB-435s cells.

Taken together, these data shows that SK2/SK3 channels are involved in MDA-MB-435s migration and regulate migration by polarizing membrane potential to values close to EK. The increase of epithelial cell migration mediated by SK channels would then be the result of an increased $K^+$ efflux and subsequent shift of the membrane potential to more negative values, leading to $Ca^{2+}$ entry through voltage-independent $Ca^{2+}$ channels.

Example 2

SK3 Protein Channel is Expressed in MDA-MB-435s Cells and in Breast Tumor Tissues To further investigate the role of SK2/SK3 channels in MDA-MB-435s cell migration, RT-PCR and Western blot analyses were performed. Central nervous system tissues, known to highly express SK channels, particularly SK3 channel, was used as a positive control. As shown in FIGS. 3A and 3B, MDA-MB-435s expressed both SK2 and SK3 channels.

SK1 gene expression was found in human CNS but not in MDA-MB-435s (FIG. 3A). In contrast, SK4 gene expression was found in MDA-MB-435s but only slightly in human CNS (FIG. 3A). This is in agreement with other works showing that if SK1 is principally expressed in central neurons SK4 expression is restricted outside of the brain.

It has been next examined whether SK2/SK3 proteins are also expressed in immortalized (MCF-10A, 184A1) or in cancerous (MDA-MB-231, T47D, SKBR3) mammary epithelial cell lines. As shown in FIG. 3B, SK2 was expressed in all cell lines. In contrast, SK3 protein was solely expressed in MDA-MB-435s cells. SK3 exhibited a membrane location as analysed by immunocytochemical experiments (Data not shown).

All the immortalized (MCF-10A, 184A1) or cancerous (MDA-MB-231, T47D, SKBR3) mammary epithelial cells, which exhibit low migrating capacity compared to MDA-MB-435s, are insensitive to apamin treatment (data not shown), thus confirming that SK3 involvement, but not the sole expression of SK2, is necessary to MDA-MB-435s migration process.

Finally, the protein expression of SK2 and SK3 channels has been analyzed in tumor and non-tumor breast tissues. As SK3 and SK2 antibodies were unsuitable for immunohistochemical experiments, the inventors were unable to test for the presence of SK channels in frozen or paraffin-embedded biopsies. Using Western blot analyses, it has been found that, as observed in mammary epithelial cancer cells, SK3 was only observed in tumor breast biopsies while SK2 protein was found in both tumor and non-tumor breast tissues (Data not shown).

Thus, SK3 channel consists of a new marker of malignant transformation of mammary epithelial cell, likely related to in vivo invasiveness.

Example 3

Figure 4A:
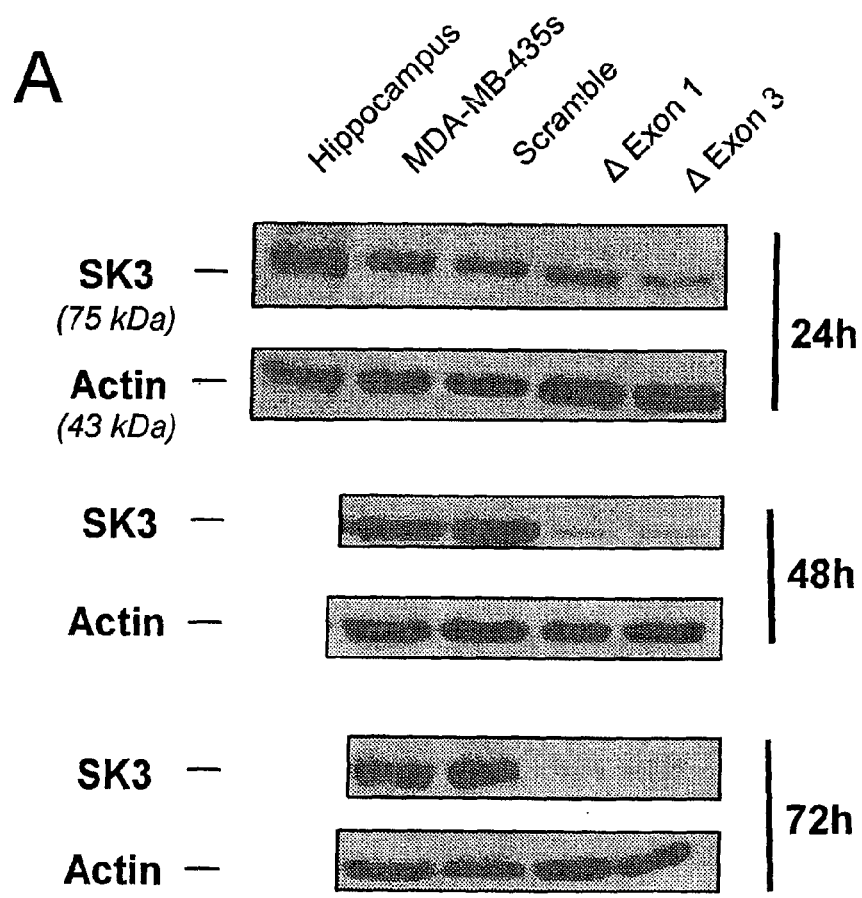
Figure 4A:
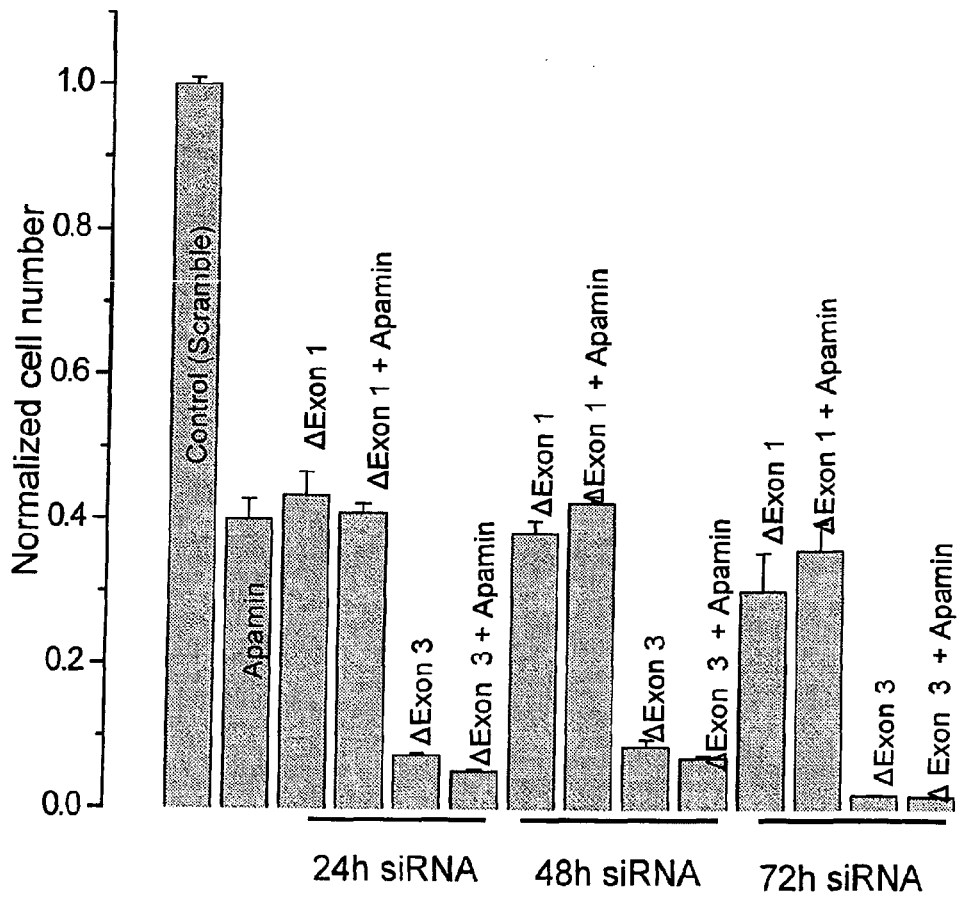
Figure 4B:
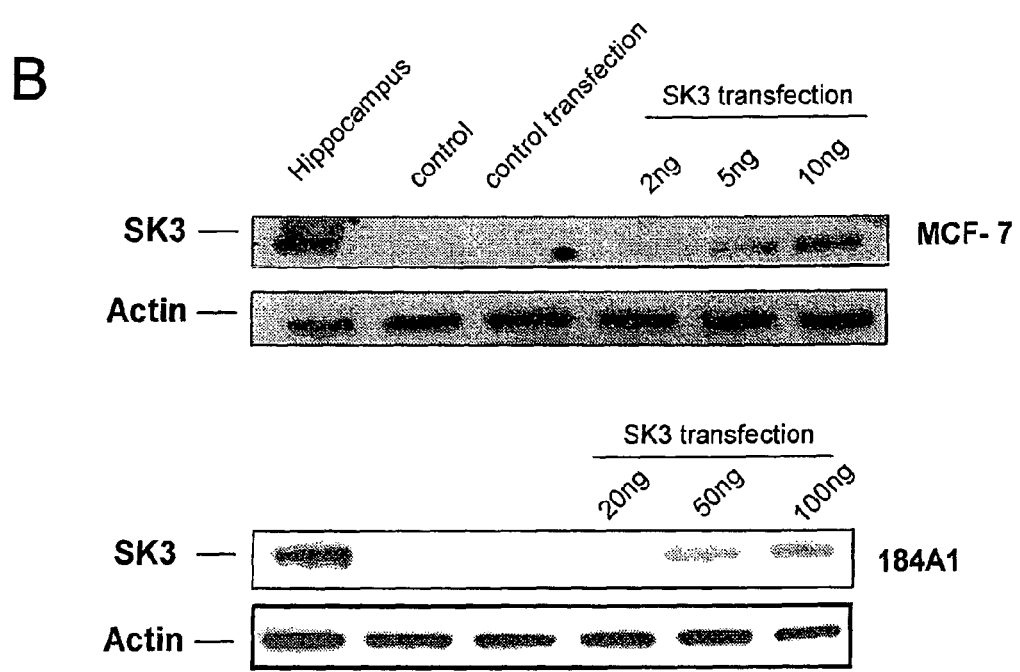
Figure 4B:
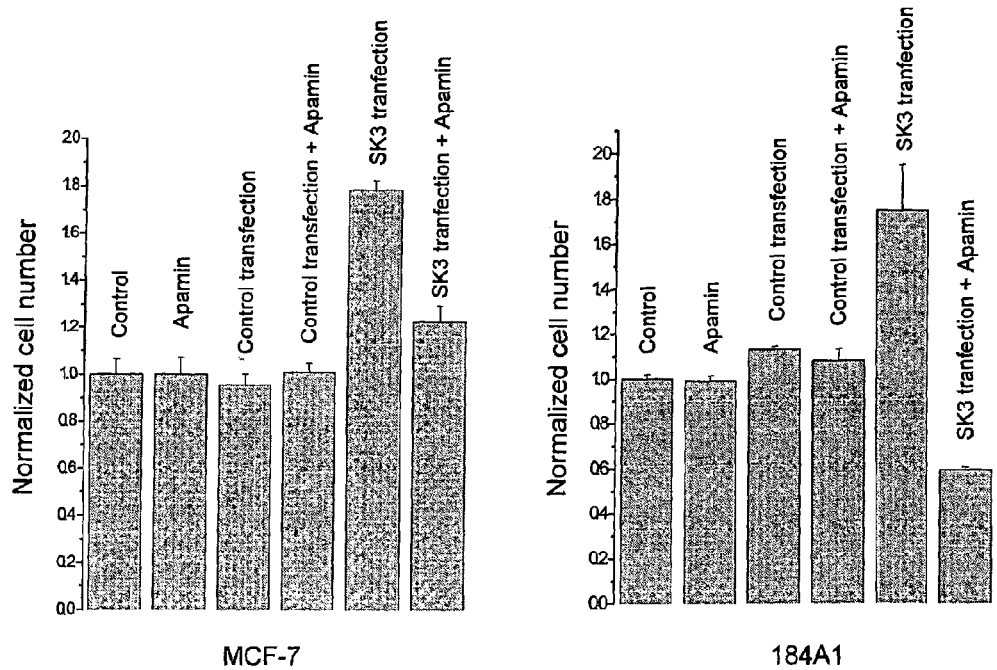

While SK3 Gene Transcript Destruction Decreased Migration of MDA-MB-435s, Enforced SK3 Gene Expression Increased Migration of MCF-7 and 184A1 Cells To fully demonstrate the contribution of SK3 protein to MDA-MB-435s migration, SK3 mRNA were knocked down by transiently transfecting cells with two different sets of siRNA locating in exon 1 (ΔExon1) or exon 3 (ΔExon3) of SK3 human gene, or with scrambled-siRNAs as a negative control. Western blot analysis and in vitro cell migration test were done 24, 48, and 72 hours after siRNAs transfection. FIG. 4A (Top) shows a marked suppression of SK3 expression in cells after transfection with both SK3-siRNAs, when compared with cells transfected with scrambled-siRNA, with the greatest effect observed at 72 hours. As expected, the knockdown of SK3 markedly reduced the number of MDA-MB-435s migrating cells (FIG. 4A, bottom). Note that, as observed with the Western blot, ΔExon3-siRNA was more efficient than ΔExon1-siRNA. The reason why efficiency is different remains to be elucidated. Previous reports described several SK3 mRNA variants with distinct sequences for exon 1 that encode SK3 proteins with distinct N-termini (Tomita H, Shakkottai V G, Gutman G A, et al. Novel truncated isoform of SK3 potassium channel is a potent dominant-negative regulator of SK currents: implications in schizophrenia. Mol Psychiatry 2003; 8:524-35, 460. Kolski-Andreaco A, Tomita H, Shakkottai V G, et al. SK3-1C, a dominant-negative suppressor of SKCa and IKCa channels. J Biol Chem 2004; 279:6893-904.). It is not excluded that high ΔExon3-siRNA efficiency is due to the full targeting and silencing of SK3 isoforms, in contrast to ΔExon1-siRNA. Nevertheless, both siRNAs are specific to SK3 protein channel, as the residual migrating capacity of cells is unaffected by apamin (FIG. 4A, bottom). These data further demonstrate that endogenous SK3 channel is necessary for MDA-MB-435s migration.

To further validate this unusual physiological activity of SK3 channel, it has been searched whether enforced SK3 expression might promote migratory capacity to cells lacking the SK3 channel. This question has been addressed by transiently transfecting SK3 in MCF-7 and 184A1 cell lines. As demonstrated in FIG. 4B, overexpression of the SK3 channel increased the number of migrating cells. Furthermore, upon treatment with the SK3 inhibitor apamin, the number of migrating cells was markedly decreased, strengthening the observed association between SK3 and cell migration capacity.

In conclusion, the novel SK3 function presented here, taken together with the intrinsic SK3 channel expression in human breast cancer, shows that the SK3 channel is a novel therapeutic target and/or new molecular marker of breast epithelial tumor.

Example 4

Involvement of SKCa Channels in Melanoma Cell Migration

The results of the previous examples demonstrated that SKCa channels and particularly SK3 channel are involved in cell migration (Potier M, Joulin V, Roger S, et al. Identification of SK3 channel as a new mediator of breast cancer cell migration. Mol Cancer Ther 2006; 5.2946-53.). Since melanoma is an extremely aggressive disease with high metastatic potential, the involvement of SK3 channels in melanoma cell migration was studied.

The effect of apamin on migration of several melanoma cell lines, Bris, 518A2, and SKmel-28 and of non cancerous melanocyte (NHEM) was tested Apamin blocks SK2 and SK3 channels at low concentration (1 nM), and does not affect SK1 and SK4 channels (Kohler M, Hirschberg B, Bond C T, et al. Small-conductance, calcium-activated potassium channels from mammalian brain. Science 1996; 273:1709-14; Liegeois J F, Mercier F, Graulich A, Graulich-Lorge F, Scuvee-Moreau J, Seutin V. Modulation of small conductance calcium-activated potassium (SK) channels: a new challenge in medicinal chemistry. Curr Med Chem 2003; 10:625-47). As shown in FIG. 5, apamin decreases migration of Bris and 518A2 cells but not of SKmel-28 and NHEM cells.

Apamin has no effect on cell proliferation/viability (data not shown). Since no specific SK3 channel blocker is available, we were unable to prove the involvement of SK3 by this approach.

To measure SKCa channels activity in melanoma cells, we performed patch-clamp experiments. FIG. 6A shows typical examples of whole-cell outward currents recorded in 518A2 cells. These outward currents showed no apparent time-dependence which is one characteristic of all SKCa currents. To study the possible involvement of SKCa channels in these epithelial cells, we tested previously describe blocker of SKCa channels, apamin. As illustrated in FIG. 6, apamin decreased 518A2 outward currents and the effect was reversible.

Example 5

Expression of SK3 Protein Channel in Melanoma Cells

To further investigate the role of SK3 channel in melanoma cell migration, Western blot analyses were performed. As shown in FIG. 7, 518A2 and Bris cells expressed both SK2 and SK3 protein. In contrast, SKmel28 cells did not expressed SK3 protein. These experiments demonstrated that apamin decrease melanoma cell migration only in cells expressing SK3 protein.

We next examined whether SK2/SK3 proteins are also expressed in melanocytes. As shown in FIG. 7 AB, SK2 and SK3 proteins were expressed in melanocytes. This result is surprising because we demonstrated that the migration of these cells was not sensitive to apamin. This suggests that in contrast to melanoma cells, the sole expression of SK3 protein in melanocyte is not sufficient to confer a migration dependant of SK3 channel.

Example 6

Induction of a Decreased Migration of Melanoma Cells by the Destruction of the SK3 Gene Transcript To fully demonstrate the contribution of SK3 protein to 518A2 migration, SK3 mRNA were knocked down by transiently transfecting cells with siRNA locating in exon 1 of SK3 human gene, or with scrambled-siRNAs as a negative control. Western blot analysis and in vitro cell migration test were done 48 hours after siRNAs transfection. FIG. 8A shows a decrease of SK3 expression in cells after transfection with SK3-siRNA, when compared with cells transfected with scrambled-siRNA. As expected, the knockdown of SK3 markedly reduced the number of 518A2 migrating cells (FIG. 8B). Our data further demonstrate that endogenous SK3 channel is necessary for 518A2 migration.

In the Enclosed Sequence Listing:
  SEQ ID No. 1 to 4 are several amino acid sequence corresponding to variants of SK3 from Homo sapiens
  SEQ ID No. 5 to 8 are polynucleotides used for RNAi experiments
  SEQ ID No. 9-12 are polynucleotides used as primers for amplifying SK3
  SEQ ID No. 13-15 are used as control.

The invention claimed is:

1. A method for the in vitro screening of an anti-metastatic compound that inhibits SK3 activity comprising:
   (a) incubating a candidate compound to be tested with SK3;
   (b) assaying for the binding of the candidate compound to be tested with SK3;
   (c) selecting positively a candidate compound if said candidate compound binds to SK3;
   (d) contacting a cell expressing a functional SK3 with said candidate compound and measuring the level of SK3 activity using a cell migration assay;
   (e) comparing the level of SK3 activity which is measured at step (d) with the level of SK3 activity which is measured when step (d) is performed in the absence of said candidate compound,
   wherein a decrease of SK3 activity in the presence of the candidate compound indicates that the candidate consists of an anti-metastatic compound.

2. The method according to claim 1, wherein the cell migration assay comprises comparing the cell to other cells expressing SK3 by the steps of:
   bringing into contact cells expressing SK3 with a membrane possessing pores sufficiently large to allow for the cells to pass through; and
   quantifying the cells that pass through the membrane, wherein the cells passing through the membrane have a SK3 activity.

* * * * *